(12) United States Patent
Grant et al.

(10) Patent No.: US 11,654,159 B2
(45) Date of Patent: May 23, 2023

(54) THERAPEUTIC USE OF ELECTROACUPUNCTURE-INDUCED MESENCHYMAL STEM CELLS

(71) Applicant: UNIVERSITY OF FLORIDA RESEARCH FOUNDATION, INC., Gainesville, FL (US)

(72) Inventors: Maria A. Grant, Archer, FL (US); Tatiana E. Salazar, Indianapolis, IN (US); Huisheng Xie, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 1263 days.

(21) Appl. No.: 16/092,119

(22) PCT Filed: Apr. 6, 2017

(86) PCT No.: PCT/US2017/026358
§ 371 (c)(1),
(2) Date: Oct. 8, 2018

(87) PCT Pub. No.: WO2017/177002
PCT Pub. Date: Oct. 12, 2017

(65) Prior Publication Data
US 2019/0117699 A1    Apr. 25, 2019

Related U.S. Application Data

(60) Provisional application No. 62/319,239, filed on Apr. 6, 2016.

(51) Int. Cl.
*A61K 35/28* (2015.01)
*A61H 39/00* (2006.01)
(Continued)

(52) U.S. Cl.
CPC .......... *A61K 35/28* (2013.01); *A61H 39/002* (2013.01); *A61H 39/086* (2013.01);
(Continued)

(58) Field of Classification Search
CPC .... A61K 35/28; A61K 9/0019; A61K 38/193; A61K 38/20; A61H 39/002;
(Continued)

(56) References Cited

U.S. PATENT DOCUMENTS 6,261,549 B1    7/2001  Fernandez et al.
2014/0214113 A1*  7/2014  Greiner ............. A61N 1/36107
                                                          607/45

FOREIGN PATENT DOCUMENTS

WO    2011069121 A1    6/2011

OTHER PUBLICATIONS

Bailey, J.L., et al. Collagen oligomers modulate physical and biological properties of three-dimensional self-assembled matrices. Biopolymers 95, 77-93 (2011).
(Continued)

*Primary Examiner* — Mark W. Bockelman
(74) *Attorney, Agent, or Firm* — Timothy H. Van Dyke; Wolter, Van Dyke, Davis, PLLC

(57) ABSTRACT

Stimulation using EA of LI-4, LI-11, GV-14 and GV-20 in humans, horses, and rodents results in mobilization of MSCs into systemic circulation. Methods are provided for increasing mesenchymal stem cells in the circulating blood of a mammal by contacting acupuncture points LI-4, LI-11, GV-14, and GV-20 of the mammal with a therapeutically effective amount of EA stimulation to mobilize MSCs into the circulating blood of the mammal. Methods for treating damaged tissue, specifically damaged tendons are also provided. Isolated mesenchymal stem cells made according to
(Continued)

these methods, methods of isolated them, and stem cell banks that store them are also provided.

14 Claims, 12 Drawing Sheets

Specification includes a Sequence Listing.

(51) Int. Cl.
  A61N 1/20    (2006.01)
  A61N 1/36    (2006.01)
  A61H 39/08   (2006.01)
  A61N 1/05    (2006.01)
  A61N 1/18    (2006.01)
  A61P 29/00   (2006.01)
  A61K 9/00    (2006.01)
  A61K 38/19   (2006.01)
  A61K 38/20   (2006.01)
  C12N 5/0775  (2010.01)

(52) U.S. Cl.
  CPC .......... A61K 9/0019 (2013.01); A61K 38/193 (2013.01); A61K 38/20 (2013.01); A61N 1/0502 (2013.01); A61N 1/18 (2013.01); A61N 1/20 (2013.01); A61N 1/3616 (2013.01); A61N 1/36017 (2013.01); A61P 29/00 (2018.01); C12N 5/0665 (2013.01); A61H 2203/03 (2013.01); C12N 2529/00 (2013.01)

(58) Field of Classification Search
  CPC .............. A61H 39/086; A61H 2203/03; A61N 1/0502; A61N 1/18; A61N 1/20; A61N 1/36017; A61N 1/3616; A61P 29/00; C12N 5/0665; C12N 2529/00; C12N 5/0663
  See application file for complete search history.

(56) References Cited

OTHER PUBLICATIONS

Baumgarth, N. & Roederer, M. A practical approach to multicolor flow cytometry for immunophenotyping. Journal of immunological methods 243, 77-97 (2000).

Bhangoo, S.K., et al. CXCR4 chemokine receptor signaling mediates pain hypersensitivity in association with antiretroviral toxic neuropathy. Brain, behavior, and immunity 21, 581-591 (2007).

Broxmeyer, H.E., et al. Rapid mobilization of murine and human hematopoietic stem and progenitor cells with AMD3100, a CXCR4 antagonist. The Journal of experimental medicine 201, 1307-1318 (2005).

Bull, N.D. & Martin, K.R. Concise review: toward stem cell-based therapies for retinal neurodegenerative diseases. Stem cells 29, 1170-1175 (2011).

Cai, L., et al. IFATS collection: Human adipose tissue-derived stem cells induce angiogenesis and nerve sprouting following myocardial infarction, in conjunction with potent preservation of cardiac function. Stem cells 27, 230-237 (2009).

Chamberlain, G., Fox, J., Ashton, B. & Middleton, J. Concise review: mesenchymal stem cells: their phenotype, differentiation capacity, immunological features, and potential for homing. Stem cells 25, 2739-2749 (2007).

Chen, X.M., Xu, J., Song, J.G., Zheng, B.J. & Wang, X.R. Electroacupuncture inhibits excessive interferon-gamma evoked up-regulation of P2X4 receptor in spinal microglia in a CCI rat model for neuropathic pain. British journal of anaesthesia 114, 150-157 (2015).

Ciccocioppo, R., et al. Autologous bone marrow-derived mesenchymal stromal cells in the treatment of fistulising Crohn's disease. Gut 60, 788-798 (2011).

Deng, J., et al. Bone marrow mesenchymal stem cells can be mobilized into peripheral blood by G-CSF in vivo and integrate into traumatically injured cerebral tissue. Neurological sciences : official journal of the Italian Neurological Society and of the Italian Society of Clinical Neurophysiology 32, 641-651 (2011).

Diez, H., et al. Hypoxia-mediated activation of Dll4-Notch-Hey2 signaling in endothelial progenitor cells and adoption of arterial cell fate. Experimental cell research 313, 1-9 (2007).

Duijvestein, M., et al. Autologous bone marrow-derived mesenchymal stromal cell treatment for refractory luminal Crohn's disease: results of a phase I study. Gut 59, 1662-1669 (2010).

Estes, M.L., et al. Application of polychromatic flow cytometry to identify novel subsets of circulating cells with angiogenic potential. Cytometry. Part A : the journal of the International Society for Analytical Cytology 77, 831-839 (2010).

Estes, M.L., Mund, J.A., Ingram, D.A. & Case, J. Identification of endothelial cells and progenitor cell subsets in human peripheral blood. Current protocols in cytometry / editorial board, J. Paul Robinson, managing editor . . . [et al.] Chapter 9, Unit 9 33 31-11 (2010).

Gavrilin, M.A., et al. Internalization and phagosome escape required for Francisella to induce human monocyte IL-1beta processing and release. Proceedings of the National Academy of Sciences of the United States of America 103, 141-146(2006).

Goldstein, D.S., McCarty, R., Polinsky, R.J. & Kopin, I.J. Relationship between plasma norepinephrine and sympathetic neural activity. Hypertension 5, 552-559 (1983).

Gunn, C.C., Ditchbum, F.G., King, M.H. & Renwick, G.J. Acupuncture loci: a proposal for their classification according to their relationship to known neural structures. The American journal of Chinese medicine 4, 183-195 (1976).

Hare, J.M., et al. Comparison of allogeneic vs autologous bone marrow-derived mesenchymal stem cells delivered by transendocardial injection in patients with ischemic cardiomyopathy: the Poseidon randomized trial. JAMA : the journal of the American Medical Association 308, 2369-2379 (2012).

Hong, H.S., et al. A new role of substance P as an injury-inducible messenger for mobilization of CD29(+) stromal-like cells. Nature medicine 15, 425-435 (2009).

Ingram, D.A., et al. Identification of a novel hierarchy of endothelial progenitor cells using human peripheral and umbilical cord blood. Blood 104, 2752-2760 (2004).

Ingram, D.A., et al. Vessel wall-derived endothelial cells rapidly proliferate because they contain a complete hierarchy of endothelial progenitor cells. Blood 105, 2783-2786 (2005).

Inoue, M., et al. The effect of electroacupuncture on tendon repair in a rat Achilles tendon rupture model. Acupuncture in medicine : journal of the British Medical Acupuncture Society 33, 58-64 (2015).

Ishihara, A., et al. Performance of a gravitational marrow separator, multidirectional bone marrow aspiration needle, and repeated bone marrow collections on the production of concentrated bone marrow and separation of mesenchymal stem cells in horses. American journal of veterinary research 74, 854-863 (2013).

Kassis, I., et al. Isolation of mesenchymal stem cells from G-CSF-mobilized human peripheral blood using fibrin microbeads. Bone marrow transplantation 37, 967-976 (2006).

Katayama, Y., et al. Signals from the sympathetic nervous system regulate hematopoietic stem cell egress from bone marrow. Cell 124, 407-421 (2006).

Kawada, H., et al. Nonhematopoietic mesenchymal stem cells can be mobilized and differentiate into cardiomyocytes after myocardial infarction. Blood 104, 3581-3587 (2004).

Kim, J.H., Kim, H.Y., Chung, K. & Chung, J.M. Electroacupuncture reduces the evoked responses of the spinal dorsal horn neurons in ankle-sprained rats. Journal of neurophysiology 105, 2050-2057 (2011).

(56) References Cited

OTHER PUBLICATIONS

Koo, S.T., Lim, K S., Chung, K., Ju, H. & Chung, J.M. Electroacupuncture-induced analgesia in a rat model of ankle sprain pain is mediated by spinal alpha-adrenoceptors. Pain 135, 11-19 (2008).
Koo, S.T., Park, Y.I., Lim, K.S., Chung, K. & Chung, J.M. Acupuncture analgesia in a new rat model of ankle sprain pain. Pain 99, 423-431 (2002).
Krampera, M., Pizzolo, G., Aprili, G. & Franchini, M. Mesenchymal stem cells for bone, cartilage, tendon and skeletal muscle repair. Bone 39, 678-683 (2006).
Kremer, H.P. The hypothalamic lateral tuberal nucleus: normal anatomy and changes in neurological diseases. Progress in brain research 93, 249-261 (1992).
Kumar, S. & Ponnazhagan, S. Mobilization of bone marrow mesenchymal stem cells in vivo augments bone healing in a mouse model of segmental bone defect. Bone 50, 1012-1018 (2012).
Le Blanc, K., et al. Mesenchymal stem cells for treatment of steroid-resistant, severe, acute graft-versus-host disease: a phase II study. Lancet 371, 1579-1586 (2008).
Le Blanc, K , et al. Treatment of severe acute graft-versus-host disease with third party haploidentical mesenchymal stem cells. Lancet 363, 1439-1441 (2004).
Liang, Z., Li, T., King, J. & Zhang, N Mapping thalamocortical networks in rat brain using resting-state functional connectivity NeuroImage 83, 237-244 (2013).
Lucas, □ , et al. Norepinephrine reuptake inhibition promotes mobilization in mice: potential impact to rescue low stem sell yields. Blood 119, 3962-3965 (2012).
Ma, C., et al. Similar electrophysiological changes in axotomized and neighboring intact dorsal root ganglion neurons. Journal of neurophysiology 89,1588-1602 (2003).
Martin-Ramirez, J , Hofman, M., van den Biggelaar, M , Hebbel, R.P. & Voorberg, J. Establishment of outgrowth endothelial cells from peripheral blood. Nature protocols 7, 1709-1715 (2012).
Martins, A.A., Paiva, A., Morgado, J.M., Gomes, A. & Pais, M.L. Quantification and immunophenotypic characterization of bone marrow and umbilical cord blood mesenchymal stem cells by multicolor flow cytometry. Transplantation proceedings 41, 943-946 (2009).
Maxson, S., Lopez, E.A , Yoo, D , Danilkovitch-Miagkova, A & Leroux, M.A Concise review: role of mesenchymal stem cells in wound repair Stem cells translational medicine 1, 142-149 (2012).
Mccormick, W.H. Traditional Chinese channel diagnosis myosfascial pain syndrome and metacarpophalangeal joint trauma in the horse. Journal of Equine Veterinary Science 16, 562-567 (1996).
Mendez-Ferrer, S., Battista, M. & Frenette, P.S. Cooperation of beta(2)- and beta(3)- adrenergic receptors in hematopoietic progenitor cell mobilization Annals of the New York Academy of Sciences 1192,139-144 (2010).
Mendez-Ferrer, S., Lucas, D., Battista, M. & Frenette, P.S Haematopoietic stem cell release is regulated by circadian oscillations. Nature 452,442-447 (2008).
Meng, H., Zhai, X , Hao, J.D. & Wang, H C [Intervention of electroacupuncture for patients with impaired glucose tolerance]. Zhongguo Zhen Jiu 31, 971-973.
Min, Y., Seo, J.H., Kwon, Y.B. & Lee, M.H. Effect of the position of immobilization upon the tensile properties in injured achilles tendon of rat. Annals of rehabilitation medicine 37, 1-9 (2013).
Mund, J.A., et al. Human proangiogenic circulating hematopoietic stem and progenitor cells promote tumor growth in an orthotopic melanoma xenograft model. Angiogenesis 16, 953-962 (2013).
Newman, R.E., Yoo, D., LeRoux, M.A. & Danilkovitch-Miagkova, A. Treatment of inflammatory diseases with mesenchymal stem cells. Inflammation & allergy drug targets 8, 110-123 (2009).
Paxinos, G.a.W., Charles. The Rat Brain in Stereotaxic Coordinates, (Academic Press, 2007).
Richardson, M.R., et al. Angiopoietin-like protein 2 regulates endothelial colony forming cell vasculogenesis. Angiogenesis 17, 675-683 (2014).
Ringden, O., et al. Mesenchymal stem cells for treatment of therapy-resistant graft-versus-host disease. Transplantation 81, 1390-1397 (2006).
Rogers, P.A., Schoen, A.M. & Limehouse, J. Acupuncture for immune-mediated disorders. Literature review and clinical applications. Problems in veterinary medicine 4, 162-193 (1992).
Samuels, B.C., Zaretsky, D.V. & DiMicco, J.A. Dorsomedial hypothalamic sites where disinhibition evokes tachycardia correlate with location of raphe-projecting neurons. American journal of physiology. Regulatory, integrative and comparative physiology 287, R472-478 (2004).
Shepherd, A.J., Downing, J.E. & Miyan, J.A. Without nerves, immunology remains incomplete—in vivo veritas. Immunology 116, 145-163 (2005).
Silva, J.R., Silva, M.L. & Prado, W.A. Analgesia induced by 2- or 100-Hz electroacupuncture in the rat tail-flick test depends on the activation of different descending pain inhibitory mechanisms. The journal of pain : official journal of the American Pain Society 12, 51-60 (2011).
Skarda, R.T., Tejwani, G.A. & Muir, W.W., 3rd. Cutaneous analgesia, hemodynamic and respiratory effects, and beta-endorphin concentration in spinal fluid and plasma of horses after acupuncture and electroacupuncture. American journal of veterinary research 63, 1435-1442 (2002).
Steiss, J.E., White, N.A. & Bowen, J.M. Electroacupuncture in the treatment of chronic lameness in horses and ponies: a controlled clinical trial. Canadian journal of veterinary research= Revue canadienne de recherche veterinaire 53, 239-243 (1989).
Tan, J., et al. Induction therapy with autologous mesenchymal stem cells in living-related kidney transplants: a randomized controlled trial. JAMA : the journal of the American Medical Association 307, 1169-1177 (2012).
Torres-Rosas, R., et al. Dopamine mediates vagal modulation of the immune system by electroacupuncture. Nature medicine 20, 291-295 (2014).
Toyama, P.M. & Nishizawa, M. The physiological basis of acupuncture therapy. Journal of the National Medical Association 64, 397-402 (1972).
Tyndall, A., et al. Immunomodulatory properties of mesenchymal stem cells: a review based on an interdisciplinary meeting held at the Kennedy Institute of Rheumatology Division, London, UK, Oct. 31, 2005. Arthritis research & therapy 9, 301 (2007).
Urano, K. & Ogasawara, S. A fundamental study on acupuncture points phenomena of dog body. The Kitasato archives of experimental medicine 51, 95-109 (1978).
Von Schweinitz, D. Thermographic evidence for the effectiveness of acupuncture in equine neuromuscular disease. Acupuncture in Medicine, 14-17 (1998).
Wang, Y., et al. CXCL10 controls inflammatory pain via opioid peptide-containing macrophages in electroacupuncture. PloS one 9, e94696 (2014).
Wible, J.H., Jr., DiMicco, J.A. & Luft, F.C. Hypothalamic GABA and sympathetic regulation in spontaneously hypertensive rats. Hypertension 14, 623-628 (1989).
Wilent, W.B., et al. Induction of panic attack by stimulation of the ventromedial hypothalamus. Journal of neurosurgery 112, 1295-1298 (2010).
Wu, Y., Zhao, R.C. & Tredget, E.E. Concise review: bone marrow-derived stem/progenitor cells in cutaneous repair and regeneration. Stem cells 28, 905-915 (2010).
Xie, H., Colahan, P. & Ott, E.A. Evaluation of electroacupuncture treatment of horses with signs of chronic thoracolumbar pain. Journal of the American Veterinary Medical Association 227, 281-286 (2005).
Zeng-bin Ma, Y.-y.Z , Liang-xiao Ma, Nan-nan Guo, Chun Li, Yan-ping Wang, Kai Cheng, Huan Yang, Wan-ning Liu, Kim Leo Wi, Jiang Zhu. Clinical Studies on the Indications of 33 Acupoints. Medical Acupuncture 20, 269-275 (2008).
Zhang, Y., et al. Electroacupuncture inhibition of hyperalgesia in an inflammatory pain rat model: involvement of distinct spinal serotonin and norepinephrine receptor subtypes. British journal of anaesthesia 109, 245-252 (2012).

(56) References Cited

OTHER PUBLICATIONS

Zijlstra, F.J., van den Berg-de Lange, I., Huygen, F.J. & Klein, J. Anti-inflammatory actions of acupuncture. Mediators of inflammation 12, 59-69 (2003).
PCT/US2017/026358; Search Report and Written Opinion, dated Aug. 16, 2017, 15 pages.
Moldenhauer, S. et al., "Mobilization of CD133(+)CD34(−) cells in healthy individuals following whole-body acupuncture for spinal cord injuries", J. Neurosci Res., 2010, vol. 88 (8) pp. 1645-1650.
Liu, Z. et al., "A New Combined Therapeutic Strategy of Governor Vessel Electro-Acupuncutre and Adult Stem Cell Transplantation Promotes the Recovery of Injured Spinal Cord", Current Medicinal Chemistry, 2011, fol. 18, pp. 5165-5171.
Liu, L et al., "Electro-Acupuncture Promotes Endogenous Multipotential Mesenchymal Stem Cell Mobilization into the Peripheral Blood", Cell Physiol Biochem, 2016, vol. 38, pp. 1605-1617.
Ho, Tsung-Jung et al., "The Possible Role of Stem Cells in Acupuncture Treatment for Neurodegenerative Diseases: A Literature Review of Basic Studies", Cell Transplantation, 2014, vol. 23, pp. 559-566.
Liu, L. et al., "Mesenchymal Stromal Cells with Immunosuppressive Potential Can Be Mobilized into Peripheral Blood by Electro-Acupuncture", Blood, 21011, vol. 118 (21), p. 4805 abstract.
EP17779824.6; Search Report, dated Nov. 18, 2019, 11 pages.

\* cited by examiner

A

B

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: primer sequence

<400> SEQUENCE: 1
ccactaccaa gaagggatct atca                24

<210> SEQ ID NO 2
<211> LENGTH: 23
<212> TYPE: DNA
<213> ORGANISM: Artificial Sequence
<220> FEATURE:
<223> OTHER INFORMATION: primer sequence

<400> SEQUENCE: 2
gggcagggtc agtcagtcaa gtc                23

<210> SEQ ID NO 3
<211> LENGTH: 20

```
<212> TYPE: DNA
<213> ORGANISM: Artificial Sequence
<220> FEATURE:
<223> OTHER INFORMATION: primer sequence

<400> SEQUENCE: 3
tcatgaagtc catggcaaga                                        20

<210> SEQ ID NO 4
<211> LENGTH: 20
<212> TYPE: DNA
<213> ORGANISM: Artificial Sequence
<220> FEATURE:
<223> OTHER INFORMATION: primer sequence

<400> SEQUENCE: 4
cttgtgccaa ctgcttttga                                        20
```

THERAPEUTIC USE OF ELECTROACUPUNCTURE-INDUCED MESENCHYMAL STEM CELLS

BACKGROUND

Intrinsic to all organisms is either the ability to regenerate or repair following injury. In lower species, regeneration is the predominant paradigm. In more complex species, the process of repair occurs instead. Strategies to optimize or activate endogenous repair mechanism during human disease would represent a critical addition to current practice. In recent years mesenchymal stem cells (MSCs) have garnered great interest for use in tissue regeneration and repair. However, their levels are essentially undetectable in the blood of healthy humans. A need exists for increasing the levels of MSCs in the blood of mammals for therapeutic use.

SUMMARY

Embodiments of the invention include a method of increasing MSCs in the blood of a mammal comprising contacting two or more acupuncture points selected from the group consisting of LI-4, LI-11, GV-14, and GV-20 (See FIG. 12) on the mammal with a therapeutically effective amount of EA stimulation to mobilize MSCs into the blood of the mammal. In a specific embodiment, contacting acupuncture points comprises inserting a needle at these points and applying electrical current to the needle. Another method relates to treating damaged tissue in a subject by increasing circulating MSCs via contacting the two or more acupuncture points with a therapeutically effective amount of EA.

Further embodiments of the invention include a method of isolating MSCs from the blood of a mammal who has undergone an electroacupuncture therapy as described herein to yield EA-mobilized MSCs. In a specific embodiment related to humans, cells are obtained that positively express markers selected from the group consisting of: CD44, CD71, CD184, and CD105, but do not express CD34. In a specific embodiment, the method includes (a) contacting acupuncture points LI-4, LI-11, GV-14, and GV-20 on the mammal with a therapeutically effective amount of EA-induced stimulation; (b) collecting the blood from the mammal after stimulation; (c) separating PBMCs from the blood and exposing the cells to conditions that expand MSCs to produce an expanded MSC population. Conditions to expand MSCs include plating the PBMCs and exposing the cells to a MSC medium, such as a combination of Ham's F-12 and DMEM in a 1:1 ratio. Final medium had 15% Fetal Bovine Serum. In a specific embodiment, the contacting step comprises contacting each of the acupuncture points at overlapping times.

Further embodiments of the invention include isolated and substantially purified MSC population expanded from the EA-mobilized MSCs and compositions comprising them made according to the methods described above, in this paragraph, and throughout the specification. Preferably, the expanded MSCs of embodiments of the invention are at least 80% pure, at least 85% pure, at least 90% pure, at least 95% pure, at least 97% pure, at least 98% pure, at least 99% pure, at least 99.5% pure, or at least 99.9% pure stimulated MSCs. The EA-mobilized MSCs possess identifiable gene expression profiles, morphology, and/or differentiation potential.

The EA-mobilized MSCs of the invention and the methods described above, in this paragraph, and throughout the specification can be human cells, horse cells, dog cells, cat cells, bovine cells, porcine cells, murine cells, and rat cells. In some embodiments, the isolated EA-mobilized MSCs may be stored in a stem cell bank.

Embodiments of the invention also include a method of treating damaged tissue in a mammal comprising contacting the damaged tissue with the isolated MSC population described in the above paragraph and throughout the specification. This contacting can be administration by direct injection into the area of the damaged tissue, or by intrathecal injection, intramuscular injection, or by intravenous injection, intra-peritoneal, or by local administration at the site of need.

Embodiments of the invention include treatment of damaged tissue as a result of injury, or trauma, or disease, or the result of acute inflammation or chronic inflammation.

Specific embodiments are directed to a method of treating damaged musculoskeletal tissue in a mammal comprising contacting the damaged tissue with the expanded MSC population described in the above paragraph and throughout the specification. This contacting can be administration by direct injection into the area of the damaged tissue, or by intrathecal injection, or by intravenous injection.

These and other features, aspects, and advantages of the present invention will become better understood with regard to the following description, appended claims, and accompanying figures.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 1A: Equine PMBCs show an increased colony-forming ability post administration of acupuncture compared to cells obtained from horses that underwent mock treatment. FIG. 1B: EA-mobilized cells demonstrated high proliferative capacity, when plated in a single-cell assay, with over 50% of them proliferating into large colonies. FIG. 1C: Following culture with osteogenic induction media, the mobilized equine cells showed strong osteogenic potency, demonstrated by Alizarin Red staining of calcium deposits (Red: Alizarin Red). Human mesenchymal cells responded in a similar fashion when cultured under identical conditions. FIG. 1D: When equine cells were incorporated into a 3D type I pig skin collagen plug with hECFC and placed under the skin of NOD/SCID mice, a large number of arteriole-like structures were observed (magnification: 40×). E) FIG. 1E: the hECFC-MSC combination had a significant increase of arteriogenesis compared to hECFC alone (MSC=equine MSC, p=0.02). FIG. 1F: After 48 hours in vitro, cells were isolated and total mRNA was extracted. Hey2 expression levels were elevated in the mixed cell treatment when compared to ECFC alone (p=0.006, n=3 for all assays).

FIG. 2A: Principal component analysis. FIG. 2B: Heat map of the hierarchical clustering (Euclidean algorithm). The EA-mobilized cells cluster in statistically different groups from MSCs derived from bone marrow, and adipose tissue, indicating a possible alternative source or stage of differentiation. FIG. 2C: Partitioning clustering (Coefficient of Shape Difference) of the genes showing statistically significant differences in expression levels in at least one comparison. Points represent the mean expression of all the genes in each cluster, per each sample, ±SEM. Clusters 1 and 4 contain genes specifically up-regulated in EA, Cluster 2 contains the genes specific for ADSC and Cluster 3 the genes specifically up-regulated in BM.

FIG. 3A: Human peripheral blood MSC ($CD44^+CD34^-AC133^-$ $CD71^+CD184^+CD105^+$ cells) measured through flow cytometry showed a significant increase in gated cell population (FIG. 3B) after treatment (p=0.017). FIG. 3C: Rat peripheral blood MSC were increased (p=0.0063) after EA. FIG. 3D: MSC were defined as Lin- cells that were positive for CD44 and Thy1. Gated cells increased post treatment. FIGS. 3E, 3F: Mice that underwent EA also showed a significant increase (p=0.008) in MSC ($PDGFR^+$ $SCA-1^+$) after treatment. Data shown as average ±SEM of percentages out of lymphocytes. FIG. 3G: Horses that received immune point EA showed a marked increase in levels of plasma NE compared to untreated horses. FIG. 3H: Rats injected with epinephrine (50 µg/kg) showed a significant elevation in MSCs in peripheral blood (p=0.0125). FIG. 3I: Injection of dopamine (50 mg/kg) for 4 consecutive days resulted in a significant increase in MSCs in blood (p=0.023), accompanied with a pointed increase in NE levels. FIGS. 3J, 3K, 3L: Pretreatment of the animals with Inderol (propranolol) inhibited MSC mobilization at 4 hours when compared to untreated animals (p=0.01).

FIG. 4A: when rat brains monitored through fMRI during administration of EA, marked activation was observed and increase in connectivity within the hypothalamus and between the hypothalamus and adjacent brain regions with progression of treatment. FIG. 4B: Rats underwent injections of a vehicle, 30 pmol or 50 pmol/100 nl of the $GABA_A$ receptor antagonist bicuculline methiodide (BMI). A significant increase was increased (p=0.027) in Thy $1^+CD44H^+$ lymphocytes in the plasma 6 hour post an injection. FIG. 4C: coronal sections from the tuberal hypothalamus from rat brain.[17] Colored circles indicate injection sites (black, orange and red represent vehicle, 30 pmol and 50 pmol respectively). FIG. 4D: representative photomicrograph showing an injection site from one rat. Abbreviations: 3V, $3^{rd}$ ventricle; DMN, dorsomedial hypothalamic nucleus; f, fornix; mt, mammillothalamic tract; PeF, perifornical hypothalamus; PH, posterior hypothalamic nucleus; ventromedial hypothalamic nucleus. Data presented as mean±SEM.

FIG. 5A-5C are bar graphs showing EA improves healing in rat pain and injury models. FIG. 5A: Effects of EA application on pain behavior in rats at 7, 9, and 14 days after partial tendon rupture in the right hind leg. Pain levels were determined by measuring the change in mN force weight-bearing forces on the affected limb. Change in the hind paw tactile threshold (in millinewtons, mN) of the ipsilateral and contralateral paw at least 18 hours after the rodent was treated at EA acupoints or EA sham acupoints every other day. Two-way ANOVA with repeated measures over time was undertaken for the tendon-injured animals. For the EA acupoint treated ipsilateral paw, main effects were significant: time (p<0.01), treatment (p=0.01), and interaction (p<0.01) Bonferroni post hoc test between EA acupoints and sham EA acupoints at each time point revealed significant differences versus sham at all time points. Corresponding analysis of the contralateral paw revealed statistically significant changes at day 9 and 14. FIG. 5B: EA increases type I collagen content in injured tendons in rats at 14 days after unilateral Achilles tendon partial tenotomy. In EA treated animal (n=9), type-I collagen content was 19.7% greater in injured tendons than contralateral non-injured tendons (p=0.02, paired t-test). In contrast, there was no difference in type-I collagen content between injured and contralateral non-injured tendons in sham treated animals (n=7) (p=0.67, paired t-test).

FIG. 8A, FIG. 8B, —5×, FIG. 8C—10×).

FIG. 115A: three subjects given EA were followed up to 5 (n=2) and 6 (n=1) hours post acupuncture. In all cases, MSC numbers declined with time progression. FIG. 11B: human EA-MSCs were expanded in vitro. FIG. 11C: After undergoing adipogenesis differentiation, EA-MSCs developed fat deposits as seen by Oil Red staining (Magnification B, C—20×, and inserts—63×).

DETAILED DESCRIPTION

Figure 1:
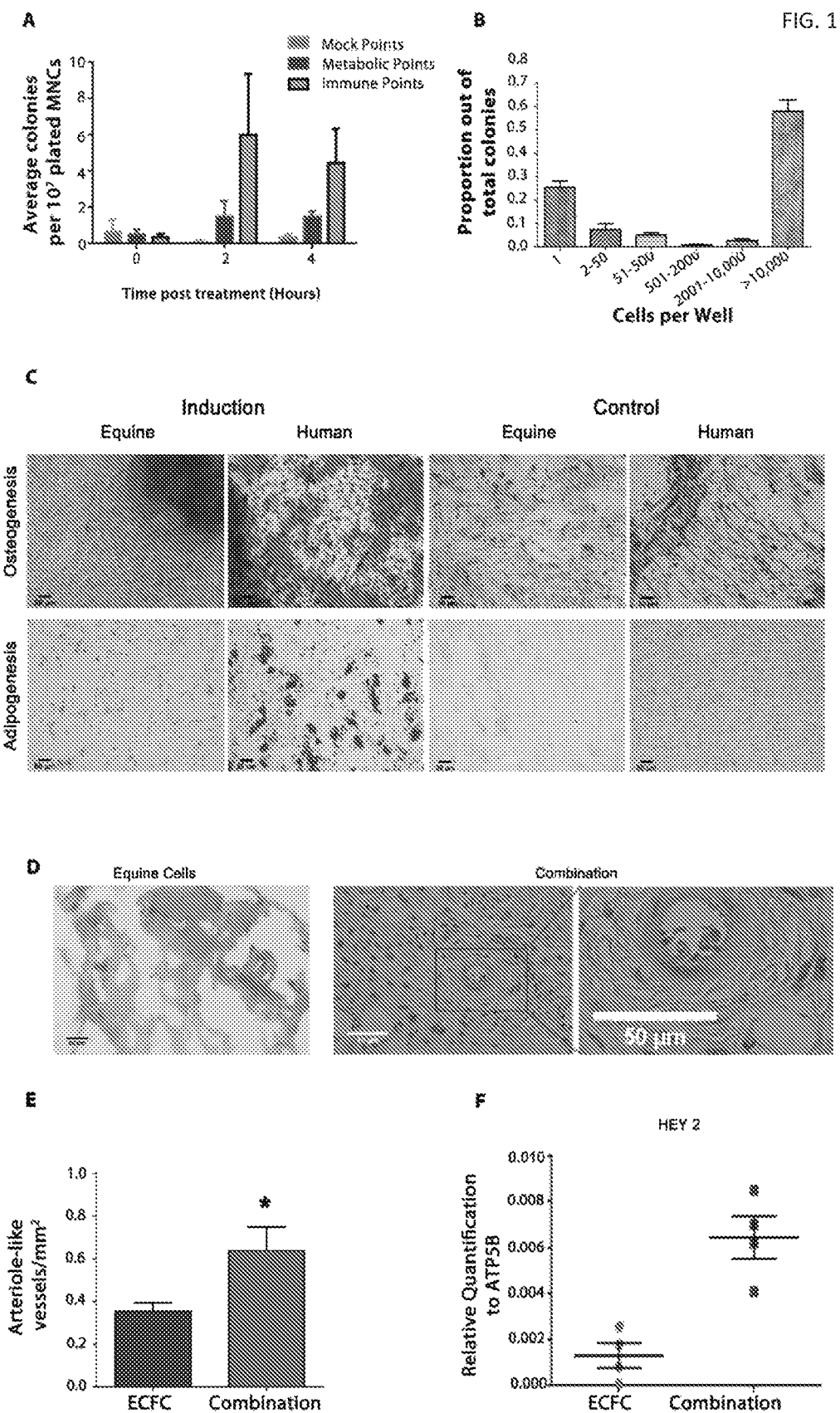
FIG. 1A-1F includes bar graphs and photographs of EA mobilized cells that were highly proliferative and differentiated into mesenchymal lineages and potentiate vasculogenesis.

It has been discovered that EA stimulation of four immune acupoints LI-4, LI11, TV-14, and GV-20 in mammals results in mobilization of MSCs into systemic circulation. It is possible to harvest these cells directly from the blood of these mammals and use the cells for collection and banking for therapeutic use in the mammal, such as damaged tendon repair.

In the following description, for the purposes of explanation, numerous specific details are set forth in order to provide a thorough understanding of the present invention. It will be apparent, however, to one skilled in the art that the present invention may be practiced without these specific details. In order that the invention may be readily understood and put into practical effect, particular preferred embodiments will now be described by way of the following non-limiting examples.

1. Definitions

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Generally, nomenclature used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ansubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwartz, Thomas M. Jessell editors. McGraw-Hill/Appleton & Lange: New York, N.Y. (2000). Unless defined otherwise, all technical and scientific terms used herein have the same meaning as commonly understood by one of ordinary skill in the art.

The term "acupuncture" as used herein, means the insertion of needles into specific points in the body (acupoints) to induce a therapeutic effect.

The term "administering" as used herein, means delivery, for example of a therapeutically effective amount of EA stimulation.

The term "carrier" as used herein, means excipients, emollients, and stabilizers or stabilizing agents or other acceptable materials, compositions, or structures involved in holding, carrying, transporting, or delivering any subject cell or composition. Each means must be "acceptable" in the sense of being compatible with the other ingredients of a subject composition and not injurious to the subject.

The term "contacting" as used herein, means bringing into close physical association or immediate proximity, including physically touching. For example, "contacting" can include exposing the acupoints LI-4, LI-11, GV-14, and GV-20 with EA-induced stimulation.

The term "detectable" refers to any amount that can be discerned by an assay or measurement system known to a person of skill in the art, above background, to a degree of statistical certainty, for example a P value of ≤0.05 as a measure of statistical significance or to any level suitable for the analysis being conducted according to standards acceptable to the person of skill in the art.

The term "electroacupuncture" or "EA" as used herein, means a form of therapeutic intervention for clinical ailments combining traditional acupuncture and modern electrotherapy. EA is quite similar to traditional acupuncture in that the same points are stimulated during treatment. As with traditional acupuncture, needles are inserted on specific points along the body. The needles are then attached to a device that generates continuous electric pulses. These devices are used to adjust the frequency and intensity of the impulse being delivered, depending on the condition being treated. EA uses more than one needle at a time so that the impulses can pass from one needle to the other.

The terms "isolated," "isolating," "purified," "purifying," "enriched," and "enriching," as used herein with respect to cells, means that the MSCs at some point in time were separated, purified, and capable of therapeutic use. "Highly purified," "highly enriched," and "highly isolated," when used with respect to cells, indicates that the cells of interest are at least about 70%, about 75%, about 80%, about 85% about 90% or more of the cells, about 95%, at least 99% pure, at least 99.5% pure, or at least 99.9% pure or more of the cells, and can preferably be about 95% or more of the MSCs.

The term "mesenchymal stem cell," or "MSC" as used herein, refers to multipotent stromal cells that can differentiate into a variety of cell types, including: osteoblasts (bone cells), chondrocytes (cartilage cells), myocytes (muscle cells) and adipocytes (fat cells).

The term "population" as used herein when used with respect to cells, means a group or collection of cells that share one or more characteristics. The term "subpopulation,"

when used with respect to cells, refers to a population of cells that are only a portion or "subset" of a population of cells.

The term "stem cell bank" as used herein means any facility that stores EA-mobilized MSCs derived from blood of a mammal for future use. MSC samples in private (or family) banks are stored specifically for use by the individual person from whom such cells have been collected and the banking costs are paid by such person.

The terms "subject," "host," and "patient," as used herein, are used interchangeably and mean a mammalian animal being treated with the present compositions, including, but not limited to, vertebrates, simians, humans, felines, canines, equines, rodents (including rats, mice and the like), bovines, porcines, ovines, caprines, mammalian farm animals, mammalian sport animals, and mammalian pets.

The terms "substantially pure," "substantially purified," and "substantially enriched" as used herein with respect to cells means the isolated cell population of mammalian MSCs that includes at least 80% pure, and preferably at least 85% pure, at least 90% pure, at least 95% pure, at least 97% pure, at least 98% pure, at least 99% pure, at least 99.5% pure, or at least 99.9% pure cells of the type in question, for example, MSCs.

As used herein, a "therapeutic agent" means a compound or molecule capable of producing an effect. Preferably, the effect is beneficial.

As used herein, "therapeutically effective amount" means an amount sufficient to treat a subject afflicted with damaged tissue as a result of injury, or trauma, or disease or an amount sufficient to reduce inflammation. The term "therapeutically effective amount" also refers to an amount sufficient to mobilize MSCs thereby increasing their number in the bloodstream of a subject.

The term "treating" as used herein, means slowing, stopping, or reversing the effects of tissue damage, and/or reducing inflammation.

2. Overview

MSCs are multipotent stromal cells that can differentiate into a variety of cell types, including: osteoblasts (bone cells), chondrocytes (cartilage cells), myocytes (muscle cells) and adipocytes (fat cells). MSCs, the major stem cells for cell therapy, have been used clinically for approximately 10 years. From animal models to clinical trials, MSCs have afforded promise in the treatment of numerous diseases, mainly tissue injury and immune disorders. MSCs are traditionally found in the bone marrow. However, MSCs can also be isolated from other tissues including cord blood, peripheral blood, fallopian tube, and fetal liver and lung. Multipotent stem cells, MSCs differentiate to form adipocytes, cartilage, bone, tendons, muscle, and skin.

Acupuncture entails the insertion of needles into specific points in the body to induce a therapeutic effect.[1-3] In human and veterinary medicine, acupuncture has been used as an accepted treatment for acute injuries and chronic medical illnesses. EA combines traditional acupuncture with modern electrotherapy with the application of a pulsating electrical current to acupuncture needles, or even without needles, to acupuncture points on the body. While the beneficial effects of EA are appreciated, the mechanism mediating these effects remains a question. While anatomical characteristics associated with specific acupoints have been proposed, no one has demonstrated a clear mechanism for the beneficial effects of acupuncture.

Here, the beneficial effects of EA were mediated by the release of MSCs into blood circulation allowing these reparative cells to increase in number and become available to injured tissue throughout the body. A mechanism is therefore provided where stimulation of the immune acupuncture points LI-4, LI-11, GV-14, and GV-20 in mammals results in mobilization of MSCs into systemic circulation.

3. Embodiments

EA stimulation of two or more acupoints LI-4, LI-11, GV-14, and GV-20 allows for mobilization of MSCs. Accordingly, methods of increasing MSCs in the blood of a mammal, isolating these MSCs or methods of treating certain injuries or conditions involving EA mobilization of MSCs, are provided. Methods for treating damaged tissue are also provided.

A. Methods of Increasing MSCs in Systemic Circulation

Based on these results, embodiments are directed to methods of increasing MSCs in blood of a mammal comprising contacting two or more acupuncture points (acupoints) of LI-4, LI-11, GV-14, and GV-20 on the mammal with a therapeutically effective amount of EA stimulation to mobilize MSCs into the blood of the mammal.

A "therapeutically effective amount," is what is sufficient to show a mobilization of MSCs thereby increasing their number in the bloodstream. The number of administrations of EA stimulation can vary. Introducing EA stimulation can be a one-time event. Alternatively, EA stimulation may be provided in a regimen that involves repeated treatments over a period of time such as daily, weekly, monthly or bimonthly, for example. The actual amount administered, at what frequency, and rate and time-course of stimulation, will depend on the age, sex, weight, of the subject, the stage of the disease, and severity of what is being treated. Decisions on EA stimulation are within the responsibility of general practitioners, scientists, and other medical doctors.

B. Methods of Isolating MSCs to Yield EA-Mobilized MSCs

Certain embodiments described herein relate to methods of isolating MSCs from the blood of a mammal to yield a MSC population that can be administered at a later time. For human samples, MSCs typically express at least one of the markers CD44, CD71, CD184, and CD105, but do not express CD34 protein. The method includes contacting two or more acupuncture points (acupoints) LI-4, LI-11, GV-14, and GV-20 on the mammal with a therapeutically effective amount of EA-induced stimulation. Blood obtained through venipuncture or other means known in the art is then collected from the mammal after stimulation. Peripheral blood mononuclear cells are separated from the blood and exposed to conditions that generate MSCs. The isolated PBMCs are plated and subjected to media suitable to support growth and expansion of MSCs. Conditions to expand MSCs include plating the PBMCs and exposing the cells to a MSC medium, such as a combination of Ham's F-12 and DMEM in a 1:1 ratio. Final medium had 15% Fetal Bovine Serum. For human samples, MSCs certain markers may assist in identifying the cells including CD44, CD71, CD184, and CD105, but not CD34.

In alternative embodiments, PBMCs may be separated from the cell suspension using any convenient method known in the art, for example, a type of flow cytometry such as fluorescence-based sorting techniques and expression labels. Suitable labels include, but are not limited to green fluorescent protein (GFP), varieties of other fluorescent proteins including yellow and red, other optical labels utilized for cell separation of PBMCs.

Techniques for labeling, sorting, fluorescence activated cell sorting (FACS) and enrichment of cells are well known in the art. Useful examples are described in WO 2001/022507 and U.S. application Ser. No. 13/391,251 (US 2012-0220030 A1), which are hereby incorporated by reference in their entirety, and specifically for their description of cell labeling, sorting, and enrichment. The cells can be identified, separated, and/or enriched based on cell markers. It will be understood by those of skill in the art that the stated expression levels reflect detectable amounts of the marker protein on the cell surface. Generally, cell markers can be assessed by staining or labeling cells with probes that specifically bind the marker of interest and that generate a detectable signal.

Culture conditions vary widely for each cell type, but the artificial environment in which the cells are cultured invariably consists of a suitable vessel containing the following: (i) a substrate or medium that supplies the essential nutrients (amino acids, carbohydrates, vitamins, minerals). (ii) growth factors, (iii) hormones, (iv) gases ($O_2$, $CO_2$), and (v) a regulated physico-chemical environment (pH, osmotic pressure, temperature). One of ordinary skill in the art could readily optimize the differentiation conditions. Recipes for media can vary in pH, glucose concentration, growth factors, and the presence of other nutrients. Classically, the control of stem cell fate has been attributed to genetic and molecular mediators (growth factors, cytokines, and transcription factors). In a specific embodiment, medium used for culturing MSCs from the PBMC sample was a combination of Ham's F-12 and DMEM in a 1:1 ratio. Final medium had 15% Fetal Bovine Serum.

One of ordinary skill in the art could readily determine the necessary components and percentages of components in an effort to optimize the medium to desired experimental protocols. As set forth below, a person of ordinary skill in the art having knowledge of the components of these types of media could optimize different concentrations of the components may be modified to arrive at desired medium including nutrients needed for long-term growth of cells. The expanded MSCs may be subjected to certain commercially available reagents to encourage differentiation into certain cell types. These reagents may include osteogenesis kit, MSC adipogenesis kit, or chondriogenesis kit sold by Millipore®, for example.

C. Isolation and Expansion of EA-Mobilized MSCs

In one embodiment, the present invention relates to an MSC population generated from the blood of a mammal using the methods described herein. The isolated MSCs may be obtained from any mammal, preferably from a human, or a horse, or a rat, or a mouse and stored in a stem cell bank, or other means of stem cell storage known to those in the art.

D. Methods of Treating Damaged Tissue

Tissue damage may be the result of injury, or trauma, or disease. In certain embodiments, the damaged tissue may be the result of acute inflammation or chronic inflammation.

EA at remote sites produces long-lasting and powerful analgesia and generation of increased type 1 collagen content indicative of tendon injury remodeling following partial rupture of the Achilles tendon. Without being bound by theory, EA-induced mobilization of MSCs may also serve to directly or indirectly modulate anti-inflammatory and immunomodulatory properties in vivo.[47,48] These effects likely limit the production of nociceptive pro-inflammatory cytokines and serve to enhance tissue remodeling following tendon injury.[16,49-51]. Further, EA treatment at immune acupoints induces mobilization of endogenous MSCs into the blood stream which migrate to a site of injury or damage and assist in repair.

In addition, MSC populations generated from an EA treated mammal as described above may be stored for later administration as needed. Accordingly, in certain embodiments, methods are provided for treating damaged tissue or damaged tendon (e.g., ruptured tendon) in a mammal comprising contacting the damaged tissue or damaged tendon with a MSC population generated from EA-mobilized MSCs as described above.

E. Compositions, Kits, and Storage

MSCs hold great promise and offer many advantages for developing effective cellular therapeutics. Current trends indicate that the clinical application of MSCs will continue to increase markedly. For clinical applications, large numbers of MSCs are usually required, ideally in a readily usable format, thus requiring extensive MSC expansion ex vivo and subsequent cryopreservation and banking. Therefore, in a certain embodiment, an MSC population generated from EA-mobilized MSCs described herein can be stored in a stem cell bank, or some other form of storage known in the art. Stem cell banking procedures and equipment is known in the art, such as that taught in U.S. Pat. No. 8,759,090 incorporated herein by reference.

The ability to preserve stem cells is critical for their use in clinical and research applications. Preservation of cells permits the transportation of cells between sites, as well as completion of safety and quality control testing. Preservation permits development of cell banks with different major histocompatibility complex genotypes and genetically modified clones. As collection of stem cells from sources such as umbilical cord blood can be difficult to predict or control, the ability to preserve cells permits the banking of stem cells until later use in the research lab or clinical application. The ability to preserve cells permits completion of quality and safety testing before use as well as transportation of the cells between the sites of collection, processing and clinical administration. Finally, the ability to preserve cells used therapeutically facilitates the development of a manufacturing paradigm for stem cell based therapies.

Losses during transfer and dilution can be minimized by using an "acceptable carrier", such as specific stabilizing agents including but not limited to heparin, platelet-derived growth factors (Yeh et al., 1993) and stem cell factors. In certain embodiments, these compositions can include EA-mobilized MSCs that are in acceptable carriers that are compatible with the EA-mobilized MSCs. Optionally, the compositions also may contain other ingredients, such as hormones or other factors which can assist in appropriate differentiation of the cells to be administered.

In certain embodiments, a composition may be administered in a number of ways either alone or in combination with other treatments, either simultaneously or sequentially depending on the condition to be treated and whether local or systemic treatment is desired. Administration may be by direct injection into the area of tissue damage, or by intrathecal injection, or intravenously, or by stereotaxic injection. The route of administration can be selected based on the disease or condition, the effect desired, and the nature of the cells being used. Actual methods of preparing dosage forms are known, or will be apparent, to those skilled in the art. (See Remington's Pharmaceutical Sciences, $20^{th}$ Edition, 2000, pub. Lippincott, Williams & Wilkins.) Where a composition as described herein is to be administered to an individual, administration is preferably in a "prophylactically effective amount" or a "therapeutically effective amount," this being sufficient to show benefit to the individual.

The number of administrations can vary. Introducing EA-mobilized MSCs in the subject can be a one-time event. Alternatively, EA stimulation may be provided in a regimen that involves repeated treatments over a period of time such as daily, weekly, bi-weekly monthly or bimonthly, for example. The actual amount administered, and rate and time-course of administration, will depend on the age, sex, weight, of the subject, the stage of the disease, and severity of what is being treated. Prescription of treatment, e.g., decisions on dosage is within the responsibility of general practitioners and other medical doctors.

MSC Compositions generated from EA-mobilized MSCs may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

4. Summary of Experimental Results

The following is a summary of results of experiments described in the Examples of this application:

- EA mobilizes colony-forming cells in peripheral blood.
- EA-mobilized cells exhibit clonogenic potential with over 75% proliferating into colonies of two more cells, and over 50% of them resulting in large colonies of 10,000 cells or more.
- EA of immune points increases the release of MSCs into the blood.
- EA-mobilized cells have MSC characteristics and can form smooth muscle cells that enhance arteriogenesis in vitro and in vivo.
- EA-mobilized MSCs have a unique gene signature compared to bone marrow derived MSC (BM-MSC) and adipose tissue-derived MSC (AD-MSC).
- Pharmacological disinhibition of the dorsomedial regions of the tuberal hypothalamus mobilizes MSC release into circulation.
- EA at remote sites produces long-lasting analgesia and generation of increased type 1 collagen indicative of tendon injury remodeling.
- EA activates the sympathetic nervous system to mobilize MSC into the circulation which can be used to enhance tissue repair and provide analgesic relief.

5. Examples

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1: Materials and Methods

Figure 9:
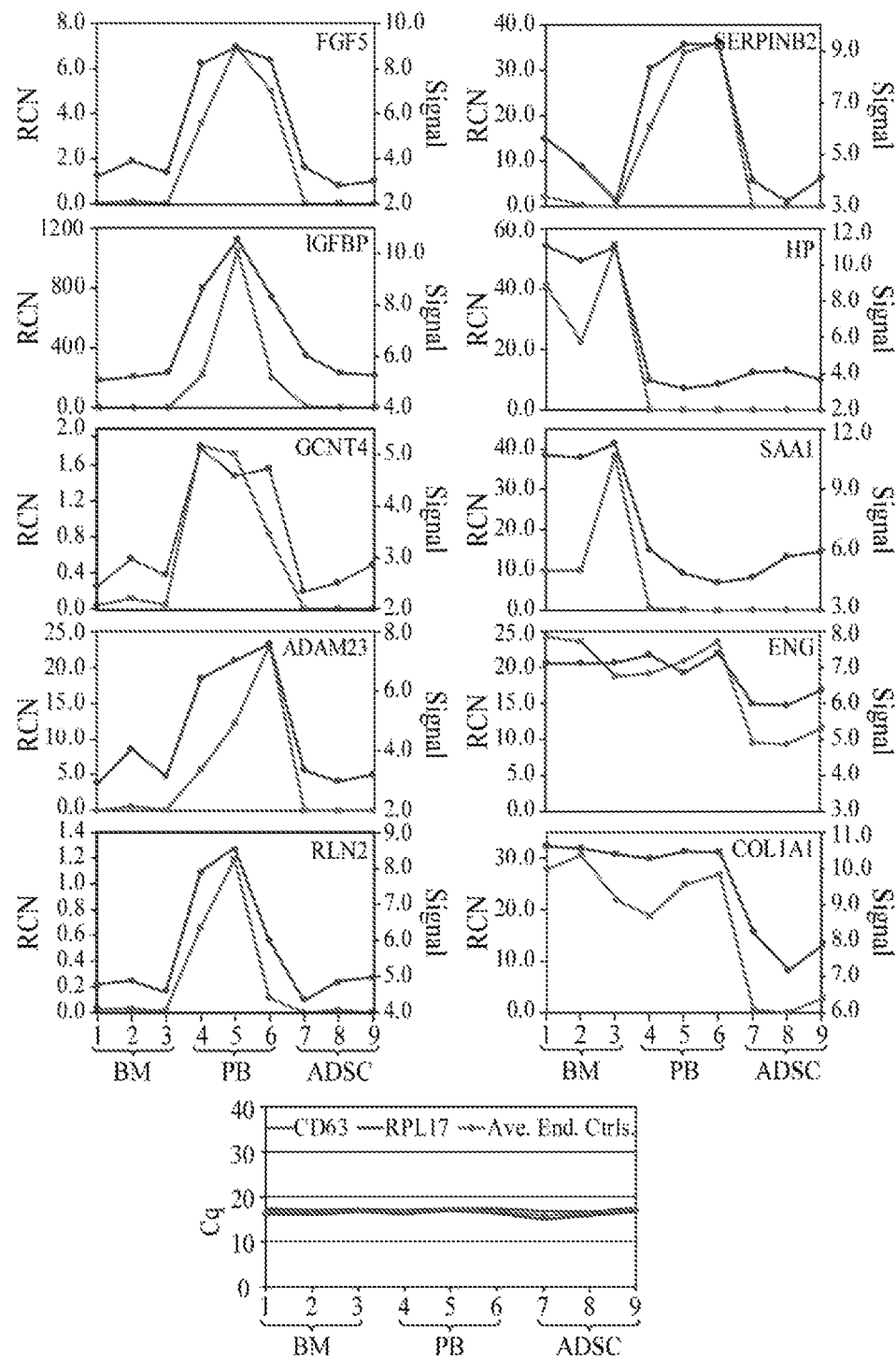
FIG. 9 are graphs showing results from qRT-PCR validation of select genes. Red: qRT-PCR data, expressed as relative copy number (RCN; left Y axis) versus the average of two control genes which were chosen based on low coefficient variation and relatively high level of expression (CD63 and RPL17). Blue: microarray data, expressed as log 2-transformed signal (Signal; Y axis). Note that the relative levels of expression vary among genes; however the patterns are the same in microarrays and qRT-PCR. The bottom panel shows the Cq for the two control genes. Note the constant expression across all samples. X axis represents in all panels the samples: BM: bone marrow-derived cells; PB: peripheral blood-derived cells; AD: adipose tissue-derived cells.

Equine Study:

Horses (n=12) undergoing treatment for different conditions (See Table S4. Characteristics of the horses used in the study) received EA at the acupoints LI-4, LI-11 and GV-14 and GV-20 (immune points) (FIG. 1). To determine the specificity of these immune points, horses received EA at BL-20, SP-6 and ST-36 (FIG. 9), common points for the treatment of metabolic diseases (metabolic points, n=4),[42] and at sham points (points not used in acupuncture, n=4), or no intervention (no acupuncture needle insertion; n=4). A fine needle (0.30 mm×75 mm, Suzhou Medical Instrument Factory, Jiangsu, China) was inserted into each acupoint. For the immune point group, six acupoints (3 sets) were used, GV-14 with GV-20, the left LI-4 with the left LI-11, and the right LI-4 with the right LI-11. Each set was stimulated by electricity with 20 Hz for 45 minutes using the EA Instrument (JM-2A model, Wuxi Jiajian Medical Instrument, Inc, Wuxi, China). For the metabolic point group, a similar experimental paradigm was utilized but the six acupoints (3 sets) were the left BL-20 with the right BL-20, the right ST-36 with the left SP-6, the right ST-36 with the right SP-6. For the sham control group, six non-acupuncture points (3 sets) were used, the left BL-20 with the spot 1 cm lateral to GV-14 with the spot 1 cm lateral to GV-20, the spot 1 cm lateral to the left LI-4 with the spot 1 cm lateral to the left LI-11, the spot 1 cm lateral to the right LI-4 with the spot 1 cm lateral to the right LI-11. Blood (30 mL/time point) was collected before EA (0 hours) and every two hours after the treatment for 6 hours (2 hours, 4 hours, 6 hours).

Figure 12:
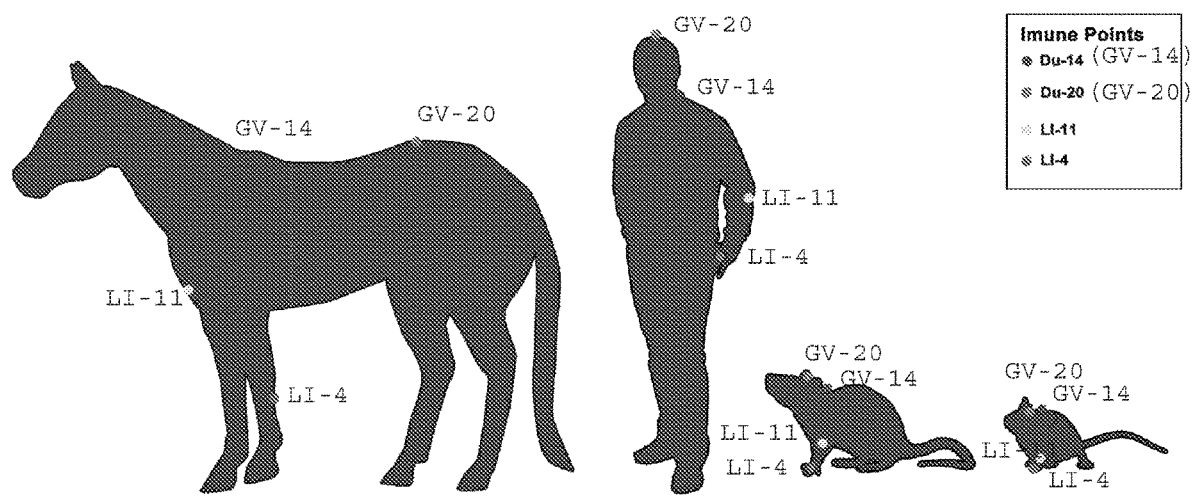
FIG. 12 is an illustration showing the location of acupuncture points in the horse, human, and rat. It will be understood that the L-11 and L-4 pertain to either a left or right side of the subject.

Human Study:

This study was done in accordance to the protocol approved by the Institutional Review Board at the University of Florida, in Gainesville, Fla. (IRB #28-2013). Informed consent was obtained prior to enrollment. Acupoints LI-4 and LI-11 were stimulated for a total of 16 minutes (FIG. 12). For all subjects, 48 mL of blood were obtained through venipuncture prior to EA (0 minutes), immediately after acupuncture and at one, two and up to 6 hours after starting treatment.

In Vitro Characterization of Mobilized Human MSC:

PBMNCs were isolated through Ficoll-Paque (GE Healthcare) gradient separation followed by Ammonium Chloride red blood cell lysis (Stem Cell Technologies). Cells were then plated at $10^7$ cells/well in uncoated, plastic 6-well plates (Thermo Scientific). Colonies appeared 21-25 days later. Cells were later collected and replated into 24-well uncoated, plastic cell culture plates (Thermo Scientific) at $6\times10^5$ cells/well and then differentiated using a Millipore Adipogenesis Differentiation Kit, as per manufacturer's protocol.

Rodent EA and fMRI Study:

All animal procedures were approved by and carried out in accordance to protocol 201207468 of the University of Florida IACUC. For administration of EA, Sprague Dawley rats or C57BL6 mice were anesthetized with 3-4% isoflurane in air for 60 seconds. The isoflurane concentration was maintained between 2 and 3% during the procedure. Animals were prepared to undergo EA, by inserting pure silver acupuncture needles (0.18×40 mm, Maeda Toyokichi Shōten, Tokyo, Japan) into the forepaws and dorsal flank at the following locations: GV-14 with GV-20, the left LI-4 with the left LI-11, and the right LI-4 with the right LI-11

(FIG. 12). For fMRI, the needles were then connected to non-magnetic wire that was inserted into the outputs of a stimulator (JM-2A model, Wuxi Jiajian Medical Instrument, Inc, Wuxi, China) designed for EA. Two wires served as opposite poles for the pairs of single points above, allowing for completion of the circuit. Baseline BOLD fMRI scans were collected for 5 minutes followed by 2 scans collected during EA stimulation (1-2 mA, 20 Hz) that lasted 45 minutes. Scans were also collected immediately following EA for a period of 13 minutes. Some rats were euthanized at baseline and others were euthanized at 2 and 4 h post completion of EA. Blood was collected and processed for flow cytometry as described below.

Tendon Rupture Model in Rats:

Partial tendon rupture was performed as described by Min et al. and followed by EA at LI-4, LI-11, and GV-14, and GV-20 as described above on every other day for 14 days.[55]

Rat Epinephrine and Dopamine Injection Study:

Sprague-Dawley rats were injected with epinephrine (SO, El Monte, Ca) intraperitoneally at 50 µg/kg. Uninjected rats were used as baseline controls. Rats were euthanized at 2, 4, and 6 hours post injection. Blood was collected and processed for flow cytometry as described below. A separate cohort of rats was injected IP with 50 mg/kg dopamine for 4 days consecutively. After last injection, rats were euthanized at 2 and 4 hours post injection. Blood was collected and processed for flow cytometry as described below.

NE, Epi, and DA Detection in Plasma:

NE levels were measured in EA-treated horses using NE ELISA kit (ALPCO™, Salem, N.H.) according to the manufacturer's instructions. Plasma NE, Epi and DA levels were measured in EA treated rats using the TriCAT ELISA kit (ALPCO™).

PBMCs Isolation:

Equine Study:

PBMCs were isolated using Ficoll-paque (GE Healthcare Biosciences, Pittsburgh, Pa.) density gradient separation and centrifuged at room temperature at 740×g for 30 minutes.

Human Study:

Blood was collected at the University of Florida, in Gainesville, Fla. (IRB #28-2013) into cell preparation tubes (CPT, BD Biosciences, California) with sodium heparin, and then spun within 2 hours of collection at 1500 RCF for 30 minutes at room temperature. After centrifugation, the cells were resuspended into the plasma and the cell suspension was sent overnight to the Angio BioCore located at Indiana University-Purdue University (IUPUI, Indianapolis) for enumeration of PBMCs and flow cytometry analysis.

Rat Study:

PBMCs were isolated using lympholyte M (Cedarlene, Ontario, Canada) density gradient separation and centrifuged at room temperature at 740×g for 30 minutes.

Cell Culture and Differentiation Assays:

Equine Blood Derived MSCs:

PBMCs were plated on uncoated, plastic, flat bottom, 6-well plates at $1 \times 10^7$ cells per well. They received a 1:1 mix of Ham's F-12 (Lonza, Basel, Switzerland) and low-glucose DMEM (Gibco®, Carlsbad, Calif.). After 96 hours, non-adherent cells were removed, and the remaining cells were maintained in medium and monitored for colony formation. Cells derived from cultures on uncoated plastic plates were expanded up to the second passage and then subjected to an Osteogenesis Assay Kit followed by Alizarin Red staining (Millipore™, Billerica, Mass.), a Mesenchymal Stem Cell Adipogenesis Kit followed by Oil Red O staining (Millipore™) and a Stem Pro® Chondriogenesis Differentiation Kit (Gibco®) followed by Alcian Blue staining to assess for differentiation along these lineages, according the manufacturer's instructions. Human BM-MSC that had been cultured for 40 days as described above for the equine cells were used as a positive control.

Images for the osteogenesis and adipogenesis assays were taken using a Zeiss Axiovert 25 inverted light microscope, at 10× magnification. Images for the chondrogenic lineages were taken using a Zeiss Axio Observer inverted microscope, at 5× and 10× magnification.

Equine Blood Derived Endothelial Colony Forming Cells (ECFC):

PBMC were placed on collagen-coated, flat bottom, 6-well plates (Rat tail-derived Collagen I, at $5.3 \times 10^{-3}$ mg/cm², BD Biosciences, San Jose, Calif.) [43] Cells were given 2 mL of complete EGM-2 (Lonza) and were allowed to settle for 72 hours with a media change every 48 hours. Total colonies were enumerated at day 10. Human cord blood endothelial colony forming cells (hECFC) were isolated and cultured as previously reported.[44]

To quantify the clonogenic potential of the mobilized ECFCs, cells grown under ECFC conditions were collected using TrypLE express (Invitrogen, Carlsbad, Calif.) and resuspended in complete EGM-2. To ensure 1 cell per well of a 96-well tissue culture plate, 66 cells were added to 10 mL EGM2 and 100 µL were added to each well precoated with type I collagen. Cells were cultured as previously described[45]. At day 14, wells were fixed with 4% formaldehyde, nuclei stained with 4',6-diamidino-2-phenylindole (DAPI) and counted using a fluorescent microscope as previously described.[45]

Equine BM Derived-MSC Generation:

BM derived-MSC were isolated from bone marrow aspirates as previously described.[46]

Equine Adipose Tissue Derived Stem Cells (ADSC) Generation:

Adipose tissue was aspirated from horse tail head fat and then digested in collagenase type I solution (Worthington Biochemical, Lakewood, N.J.). ADSC were isolated as previously published.[47]

In Vivo Angiogenesis Assay

Human ECFC and equine MSC were expanded and then assessed by an in vivo angiogenesis assay in NOD/SCID mice. Type I pig skin oligomeric collagen (PSC) and necessary reagents (HCl, PBS, NaOH, and $CaCl_2$) were generated and prepared as previously described[48]. Collagen-cell suspensions (200 cells/µL at 100 Pa) were kept at 4° C. during mixing, pipetted into wells of a 48-well plate (250 µL/well) and allowed to polymerize for 30 min. Complete EGM2 (500 µL/well) was added and plates were kept at 37° C., 5% $CO_2$ in a humidified incubator overnight. Matrix-cell constructs were then implanted into the flank of NOD/SCID mice for 14 days. The matrix-cell constructs were removed, formalin fixed, and paraffin embedded prior to tissue sectioning and staining with hematoxylin and eosin. Brightfield images were collected using a Leica DM4000B microscope with a N PLAN 40×/0•65 NA objective. Images were acquired using a SPOT RT color camera (Diagnostic Instruments, Sterling Heights, Mich.) with the manufacturer's software.

RNA Isolation, Microarray and Real-Time PCR (qRT-PCR):

RNA Isolation:

RNA was isolated using the RNeasy Micro Kit (Qiagen, Germantown, Md.) according to the manufacturer's instructions using DNAse I on column genomic DNA digestion. RNA was quantified using a Nanodrop 1000 (Thermo Scientific, Whaltman, Mass.). For the microarray assay, RNA was isolated using the RNeasy Kit (Qiagen) and quality was assessed by Agilent Bioanalyzer 2100 (Agilent Technologies, Santa Clara, Calif.).

Microarray:

100 ng total RNA were used for processing with the Ovation® RNA Amplification System V2 and Encore™ Biotin Module. Hybridization, staining and scanning of EquGene-1_0-st-v1 GeneChips® (Affymetrix, Santa Clara, Calif.) were performed using Affymetrix instrumentation (GeneChip Hyb-Station Oven 320/640, Fluidics Station 450s, and GeneChip Scanner 3000 7G) according to manufacturer's recommended protocols. BM-MSC from three equine donors, EA-MSC from three equine donors, and equine AD-MSC from 3 donors were used, for a total of nine equine GeneChips®.

Microarray Data Analysis:

After passing the quality controls, CEL files were analyzed with Affymetrix Expression Console in conjunction with Affymetrix Transcription Analysis Console, and with Partek Genomic Suite. Principal Component Analysis (PCA) followed by ANOVA was performed. Since these programs have slightly different algorithms for calculating fold-change, only the genes that had a p<0.05 and absolute value of the fold-change ≥2 (EA-MSC vs. either BM-MSC or AD-MSC) in both analyses were further examined. On these genes, hierarchical clustering (Euclidean algorithm, average linkage, done on standardized values: means=0, SD=1) and partitioning clustering (Coefficient of Shape Difference algorithm, with a choice of 4 clusters after checking a range of numbers, also done after standardization of expression values) were performed. To explore the functional coordinates of these genes, Ingenuity Pathway Analysis (IPA®, QIAGEN Redwood City, Calif.) was used. Since *Equus caballus* is not yet supported by IPA, the equine EntrezGene IDs were uploaded in BioMart Central Portal to obtain the generic WikiGene Names, which were further used as inputs for IPA, with the respective fold-change and p values.

qRT-PCR:

Reverse transcription was carried out using the Omniscript RT Kit (Qiagen, Germantown, Md.) incorporating Oligo (dT) 15 primer (Promega, Madison, Wis.). Real-Time PCR was performed using the FastStart Universal SYBR Green Master (ROX) (Roche, Basel, Switzerland) using 25 ng per reaction in an ABI7500 Real-Time PCR system (Applied Biosystems®, Carlsbad, Calif.). Cycling conditions were as follows: 95° C. for 10 minutes, followed by 40 cycles of 95° C. for 15 seconds and 60° C. for 1 minute. 7500 Software (Applied Biosystems®, Carlsbad, Calif.) was used to determine the quantification cycle (Cq) values. Data was analyzed using the $2^{-Cq}$ method using the house keeping gene ATP5B for normalization. Each sample was measured in triplicate, and a maximum standard deviation between quantification cycle (Cq) values of 0.3 was considered acceptable. Primer sequences: 1) ATP5B, F: CCACTAC-CAAGAAGGGATCTATCA, (SEQ ID NO: 1) R: GGGCAGGGTCAGTCAGTCAAGTC; (SEQ ID NO: 2) HEY2, R: TCATGAAGTCCATGGCAAGA (SEQ ID NO: 3) F: CTTGTGCCAACTGCTTTTGA (SEQ ID NO: 4).

Validation of Select Genes by qRT-PCR.

To validate the microarray findings, we tested by qRT-PCR 12 genes (Table S5. Primers used for the qRT-PCR validation of microarray data). The primers were designed using PrimerExpress v. 3.0 (Life Technologies/Applied Biosystems, Foster City, Calif.) to encompass a junction site (where possible) and were purchased from Integrated DNA Technologies (Coralville, Iowa). Reverse transcription was done starting from 400 ng RNA per reaction, using the Vilo kit (Life Technologies/Invitrogen). RT-PCR was performed using SYBR Green (Life Technologies/Applied Biosystem) in a final volume of 10 μL, in the 7900HT Real-Time PCR System (Life Technologies/Applied Biosystems) using standard cycling conditions and followed by a dissociation step. Data processing was done with Excel (Microsoft Office Professional Plus 2010) and are expressed as relative copy numbers (RCN), defined as RCN 2—Cq(reference).[49] As reference we used the average of two genes (CD63 and RPL17) which were chosen based on low coefficient of variation and relatively high level of expression on the microarrays.

Multi-Parametric Flow Cytometry Immunostaining (MPFC), Acquisition and Analysis

MPFC:

PBMCs were stained with the MPFC protocols in real-time within 24 h after blood collection at the Angio BioCore, IUPUI, for the identification of MSCs as previously described.[50-53] 23 PBMCs were incubated with Fc blocking reagent (Miltenyi Biotec or BD biosciences) for 10 minutes on ice and stained as published[50]. Cells were incubated with titrated antibodies for 30 minutes at 4° C., washed twice in PBS with 2% FBS, fixed in 1% paraformaldehyde (Tousimis, Rockville, Md.), and run on a BD LSRII flow cytometer (BD) equipped with a 405 nm violet laser, 488 nm blue laser and 633 nm red laser. Data were acquired uncompensated and exported as FCS 3.0 files, and analyzed utilizing FlowJo software, version 9.7.5 or version X (Tree Star, Inc, Ashland, Oreg.). "Fluorescent minus one" (FMO) gating controls were used to ensure proper gating of positive events[50,52,54]. In order to resolve the rare and/or dim populations of interest, specific antigen and fluorochrome conjugate coupling was optimized for the six-antibody plus a viability marker staining panel[50-54]. BD compBeads (BD Biosciences) were used for color compensations.

For human MSCs, the following primary conjugated monoclonal antibodies were used: PE-CD34, clone 581 (BD Biosciences, San Jose, Calif.), APC-AC133, clone AC133 (Miltenyi Biotec, San Diego, Calif.), FITC-CD105, clone 266 (BD Biosciences), PECy5-CD71, clone MA712 (BD Biosciences), PECy7-CD184, clone 12G5 (BD Biosciences), Horizon V450-CD45, clone HI30 (BD Biosciences), APC-H7-CD44, clone C26 (BD Biosciences), and the fixable amine reactive viability dye, LIVE/DEAD Violet Dead Cell Stain Kit, (Life Technologies/Invitrogen, Grand Island, N.Y.). Human MSC were gated sequentially on FMO gates for LIVE/DEAD$^-$CD4$^-$ CD44$^+$CD34$^-$AC133$^-$CD71$^+$CD184$^+$CD105$^+$ cells.[53]

For rat MSCs, the following primary conjugated monoclonal antibodies were used: FITC-CD44H, clone OX-49 (BD Biosciences), PECy7-CD90, clone OX-7 (BD Biosciences), biotin-CD31, clone MEC13.3 (BD Biosciences), biotin-anti erythroid cells, clone HIS49 (BD Biosciences), biotin-CD45, clone OX-1 (BD Biosciences), Horizon V450-CD11b, clone WT.5 (BD Horizon), Horizon-V450 streptavidin (BD Biosciences) and fixable viability dye efluor-780 (ebioscience). Rat MSC were gated sequentially on FMO gates for LIVE/DEAD$^-$CD45$^-$erythroid cells$^-$CD31$^-$CD11b$^-$ CD90$^+$CD44H$^+$ cells.

For mouse MSCs, the following primary conjugated monoclonal antibodies were used: PECy7-Ly6A/E, clone D7 (BD Biosciences), PE-CD44, clone IM7 (BD Biosciences), PerCP-efluor710-CD73, clone TY/11.8 (ebiosciences), AlexaFluor647-CD105, clone MJ7/18 (BD Biosciences), PE-CF594-CD140A, clone APA5 (BD Horizon), BV-421-CD11b, clone M1/70 (Biolegend), BV-421-CD45, clone 30-F11 (Biolegend), biotin-CD31, clone PECAM-1 (BD Biosciences), biotin-TER119, clone TER119 (BD biosciences), Horizon V450-CD11b, clone WT.5 (BD Horizon), Horizon-BV421 streptavidin (BD Biosciences) and fixable viability dye efluor-780 (ebioscience). Murine MSCs were gated sequentially on FMO gates for LIVE/DEAD⁻ Lin⁻ (CD45⁻TER119⁻CD31⁻CD11b⁻) Ly6A/E+ CD140A+ cells and the expression of the other MSC markers was confirmed.

Magnetic Resonance Imaging (MRI)

Stimulus free BOLD weighted scans were collected in order to investigate resting state functional connectivity as previously reported[55] Rats were anesthetized with isoflurane and kept between 1 and 1.5% during the image acquisition. Images were collected on a 4.7-Tesla Magnex Scientific MR scanner (RRI 220/115-S14 gradients with 115 mm inner gradient bore size; maximum gradient strength 670 mT/m at 300 Amps) that was controlled by Agilent Technologies VnmrJ 3.1 console software. A quadrature transmit/receive coil tuned to 200 MHz (1H resonance) was used for B1 excitation and signal detection (AIRMRI, LLC, Holden, Mass.). A spin-echo-planar-pulse-sequence with echo time of 50 ms and repetition time of 1000 ms was used for functional acquisition. The field of view was 32.5 mm$^2$ in plane and 1.5 slice, with a data matrix of 642.

Anatomical scans for image overlay and reference-to-atlas-registration was collected with a fast spin echo sequence (effective TE=45 ms, TR=2 sec, FOV=32•5 mm$^2$ in plane and 1.5 slice, with a data matrix of 642).

A seed-based approach was used for analyzing spontaneously fluctuating BOLD signals in the rat brain before, during and after acupuncture. Scans were individually skull stripped, registered to a segmented atlas of the rat brain, and motion and drift correction was applied. Images were band pass filtered (0.01-0.1 Hz) to remove high and low frequency components. Each subject was registered to a fully segmented rat brain atlas. Individual seed regions of interest (ROI) were chosen a priori from 3 major hypothalamic areas. Individual time series signals were extracted and used for correlating with the rest of the brain on a voxel-by-voxel basis using Analysis of Functional Neuro Images (AFNI, http://afni.nimh.nih.gov/afni/). Resultant maps of Pearson's correlation coefficients were Fisher's z-transformed and the final images were group analyzed using a two way ANOVA (p<0.05, FDR corrected). Monte Carlo simulations (10000 iterations) were performed with alpha threshold of 0.001 and FWHM 1.1 mm.

Pharmacological Disinhibition of the Dorsomedial Regions of the Tuberal Hypothalamus Animals Adult male Sprague-Dawley rats (300-350 g; Harlan Laboratories, Indianapolis, Ind.), were housed in plastic cages under standard environmental conditions (22° C.; 12/12 light/dark cycle; lights on at 7:00 A.M.) for 7-10 days prior to the surgical manipulations. Food and water were provided ad libitum. All experiments were conducted in accordance with the Guide for the Care and Use of Laboratory Animals, 8$^{th}$ Edition (Institute for Laboratory Animal Research, The National Academies Press, Washington, D.C., 2011) and the guidelines of the IUPUI Institutional Animal Care and Use Committee.

Surgical Procedures

Once rats were anesthetized with an isoflurane system (MGX Research Machine; Vetamic, Rossville, Ind.), they were placed in a small animal stereotaxic frame (Model 963 Ultra Precise Frame, Kopf, Tujunga, Calif.). A 26 gauge guide cannula (cat. no. C315G, Plastics One, Roanoke Va.) was unilaterally directed at sympatho-excitatory regions of the dorsomedial regions of the tuberal hypothalamus[56] based on the following stereotaxic coordinates relative to bregma (incisor bar set at +5 mm; Anterior −3.30 mm, Lateral +1.2 mm and Ventral −8.50 mm. A 33 gauge dummy cannula (cat. no. C215DC, Plastics One) was inserted into the guide cannula to prevent blockage. After at least 5 days of recovery, the dummy cannula was removed and replaced with a 33 gauge injector cannula (cat. no. C315I, Plastics One) and conscious and freely moving rats were injected with 100 nl of either sterile 0.9% saline vehicle; 30 pmoles, or 50 pmoles of the GABAA receptor antagonist bicuculline methiodide (BMI, cat. no. 40709-69-1, Sigma Aldrich, St. Louis, Mo.) at a rate of 200 nL/min using a syringe pump (cat. no. Standard PHD Ultra CP pump, Harvard Apparatus, Hollistan, Mass.). At time of euthanization, blood was removed for flow cytometry. Brains were then removed, and flash frozen in isopentance precooled with dry ice. Brains were sectioned coronally at 30 μM on a cryostat (model no. 1800, Leica, Buffalo Grove, Ill.) at −20° C., then placed on slides to dry. Injection cannula placement was verified with phase contrast 1•6×, 5×, and 20× objectives on a trinocular microscope (Lieca DMLB) with a fast acquisition digital color Camera (model no. DFC310 FX, Leica) and Leica Applications Suite Software (version 4.1.0).

Statistical Analysis:

A linear mixed model framework was used to analyze the data over time. For circulating NE levels and human MSCs the correlation between treatment and time measurements on the same subject under different conditions was taken into account. Time points 0, 2, 4, and 6 hours were used. When correlation appeared consistent over time, compound symmetry covariance structure was used. For count data, generalized mixed models, assuming a Poisson response distribution were appropriate. A p-value of less than 0•05 was considered statistically significant. When an autoregressive structure with less correlation between time points further apart was suggested by the correlation between time point over time, overall fit of the model was assessed, with pairwise comparisons between baseline and the subsequent time points.

For the studies involving pharmacological disinhibition of the dorsomedial regions of the tuberal hypothalamus, a Kruskal-Wallis non parametric ANOVA was used to analyze lymphocyte and PBMC data since these data sets were not normally distributed (respectively, Levene's=3.9, p=0.043 and Levene's=3.8, p=0.047). Posthoc analyses was done with a Dunnet's test with vehicle as control.

For the rat and mouse experiments one way ANOVA was used to compare MSC levels to baseline.

Microarray data has been deposited in GEO and given the accession number GSE53723.

Example 2: EA Mobilizes Colony-Forming Cells in Peripheral Blood

The peripheral blood of horses undergoing EA at LI-4, LI-11 and GV-14 was first examined for colony-forming ability in vitro. While colony-forming cells were rarely seen at baseline, colony-forming ability was easily detected in blood samples obtained 2 and 4 hours after EA (FIG. 1A). Blood collected with an identical time course using mock points approximately 1 cm from the immune points or using metabolic points from the same horses did not give rise to colonies in vitro. Importantly, and representing a more critical control than simple sham acupoints, the use of metabolic points similarly did not give rise to significantly more colonies in vitro.

Example 3: EA-Mobilized Cells Exhibit Clonogenic Potential

To verify the stem/progenitor characteristics of the equine cells, clonogenic potential was determined using single cell assays. Cells were plated at 1 cell per well of a 96-well plate and after 13 days, cells were enumerated using DAPI to stain nuclei. The EA-mobilized cells showed robust clonogenic potential, with over 75% proliferating into colonies of 2 or more cells, and over 50% of them resulting in large colonies of 10,000 cells or more, indicating a high capacity for self-renewal, a characteristic of stemness (FIG. 1B).

Example 4: EA of Immune Points Increases the Release of MSCs into the Blood

Figure 7:
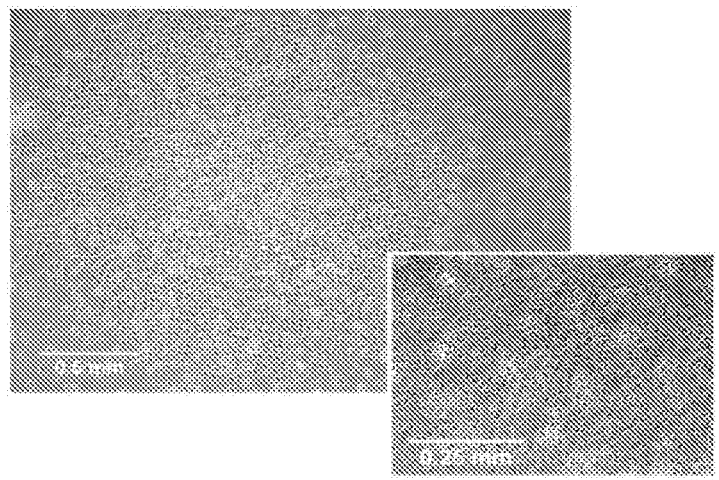
FIG. 7 is a photograph showing colonies from EA mobilized cells with MSC phenotype. PMBCs were cultured for 10 days, after which colonies were enumerated. (Magnification: Background—5×, Insert—10×).

To determine the origin of the mobilized colony forming cells, equine peripheral blood mononuclear cells (PBMCs) were placed in complete growth medium either on uncoated plastic plates for MSC identification or on type I collagen-coated plates for identification of endothelial colony forming cells (ECFC), the primary stem/progenitor population responsible for repair of the vasculature. Both conditions gave rise to MSCs and interestingly, even under ECFC conditions, no cobblestone morphology characteristic of ECFC was observed, but rather colonies of cells with mesenchymal morphology were detected between 10-14 days of culture (FIG. 7).

Figure 8:
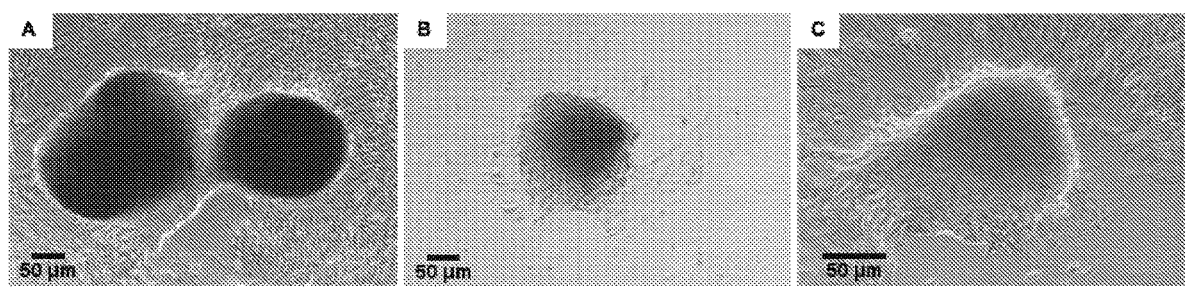
FIGS. 8A, 8B and 8C are images showing acupuncture-mobilized cells differentiating into chondrogenic lineages. When cells are cultured under chondrogenesis differentiation medium, they are able to differentiation into chondrogenic lineages, demonstrated by Alcian Blue staining of proteoglycans in the cell masses (Magnification.

Cells with MSC morphology were expanded to the second passage and then further characterized for MSC potential using in vitro assays for osteogenesis, adipogenesis and chondrogenesis, and their morphology was compared to human MSC cultures. Cells derived from horses that received EA at immune points exhibited strong osteogenic differentiation as demonstrated by positive staining for calcium deposits (FIG. 1C) compared to human MSC and control undifferentiated cells. Although the equine cells showed some adipogenic differentiation, the response was considerably weaker than the response from the human MSC but distinct from undifferentiated control cells. Equine EA-mobilized cells were also able to undergo chondrogenic differentiation (FIG. 8). The ability to differentiate along osteogenic, chondrogenic and adipocytic lines supports a mesenchymal stem cell origin.

Example 5: EA-Mobilized Cells Enhance Arteriogenesis In Vitro and In Vivo

When the EA-mobilized equine cells were examined in the in vivo angiogenesis assay, the cells did not appear to form vessels with the murine capillaries, but did statistically significantly enhance endothelial cell (EC) vasculogenesis (FIGS. 1D, 1E, and 1F). When human ECFC (hECFC) or murine ECFC are cultured in 3-D type 1 porcine collagen, they form lumenated tubes de novo in this in vitro assay.[12] EA-mobilized equine cells did not lumenize in this assay supporting their non-endothelial phenotype. However, the EA-mobilized cells significantly increased the number of arterial-like structures compared to implants containing hECFC alone in vivo. Furthermore, when the EA-mobilized MSC were co-cultured with hECFC in vitro, a significant increase in HEY2 expression was observed in the EC, which indicated that the addition of the equine cells promoted arteriogenesis, as Notch activation is known to be active in arterial vessels[13] (FIG. 1F). Overall, these data support that EA-mobilized cells have MSC characteristics and can form smooth muscle cells to enhance arteriogenesis.

Example 6: EA-Mobilized MSCs have Unique Gene Signature Compared to Bone Marrow Derived MSCs (BM-MSCs) and Adipose Tissue-Derived MSCs (AD-MSCs)

To investigate the origin of the EA mobilized MSCs, gene array studies were performed and directly compared the EA-mobilized MSCs to equine bone marrow-derived MSCs (BM-MSCs) and adipose tissue-derived MSCs (AD-MSCs).

Of the ~30,000 genes present on the EquGene-1_0-st GeneChip®, 678 showed significant differences between EA-MSCs and BM-MSCs, 1164 between the EA-MSCs and AD-MSCs and 1193 between AD-MSCs and BM-MSCs (all $p<0.05$ and absolute fold change $>2$). Both principal component analysis (PCA) mapping (FIG. 2A) and hierarchical clustering (FIG. 2B) showed that the EA-MSCs segregated into a different group from BM-MSCs and the AD-MSCs. This suggests that the EA-mobilized MSC population may be derived from a source distinct from either adipose tissue or bone marrow. Genes that were specifically upregulated in the EA-MSCs compared to BM-MSCs and AD-MSCs (FIG. 2C, partitioning clustering, clusters 1 and 4) encoded numerous proteins with roles in cell cycle control and progression, DNA replication and repair, endothelial cell physiology, and adhesion and migration (BGN, CTH, DHFR, ENG, EDN1, MYOF, PROCR, VEGF, several integrins, and SERPINB2). In addition, this group contained genes coding for enzymes implicated in extracellular matrix synthesis, such as proteoglycans (e.g., HAS2, also possibly involved in vasculogenesis, CHSY1, GCNT4, etc.) and collagens (COL1A1, COL1A2, COL3A1, COL5A1, COL5A2, COL12A1). Furthermore, EA-MSCs expressed several growth hormones, hormone receptors and members of their signaling pathways (FGF5, BDNF, HTR2A, ADORA2B, RLN) (See Table S1. Top significantly up-regulated genes in EA-mobilized MSCs as compared to bone marrow-derived (BM) MSCs and adipose-derived stem cells (ADSCs)).

When the pathways in which these genes were involved were analyzed using IPA®, the EA-MSCs expressed genes were involved in cellular growth and proliferation, hepatic pathways and embryonic stem cell pluripotency, DNA damage response, axonal guidance signaling, and cardiovascular system development. Top canonical pathways included mitotic roles of polo-like kinase, cell cycle: G2/M DNA damage checkpoint regulation, cell cycle control of chromosomal replication, GADD45 signaling and ATM signaling (Table S2. Top canonical pathways identified by ingenuity pathways analysis to be different between EA mobilized equine cells and equine BM derived MSCs).

Genes showing the greatest decreases in EA-MSC were acute-phase response genes and protease inhibitors (HP, SAA1, JAM2, C1S, C1R, SLPI), concordant with the fact that stimulation of EA points reduces acute and chronic inflammation and that the cells would require suppression of protease inhibitors to facilitate migration and mobilize from tissue depots (See Table S3. Significantly down-regulated genes in EA-mobilized MSC as compared to BM-MSC and ADSC).

Figure 2:
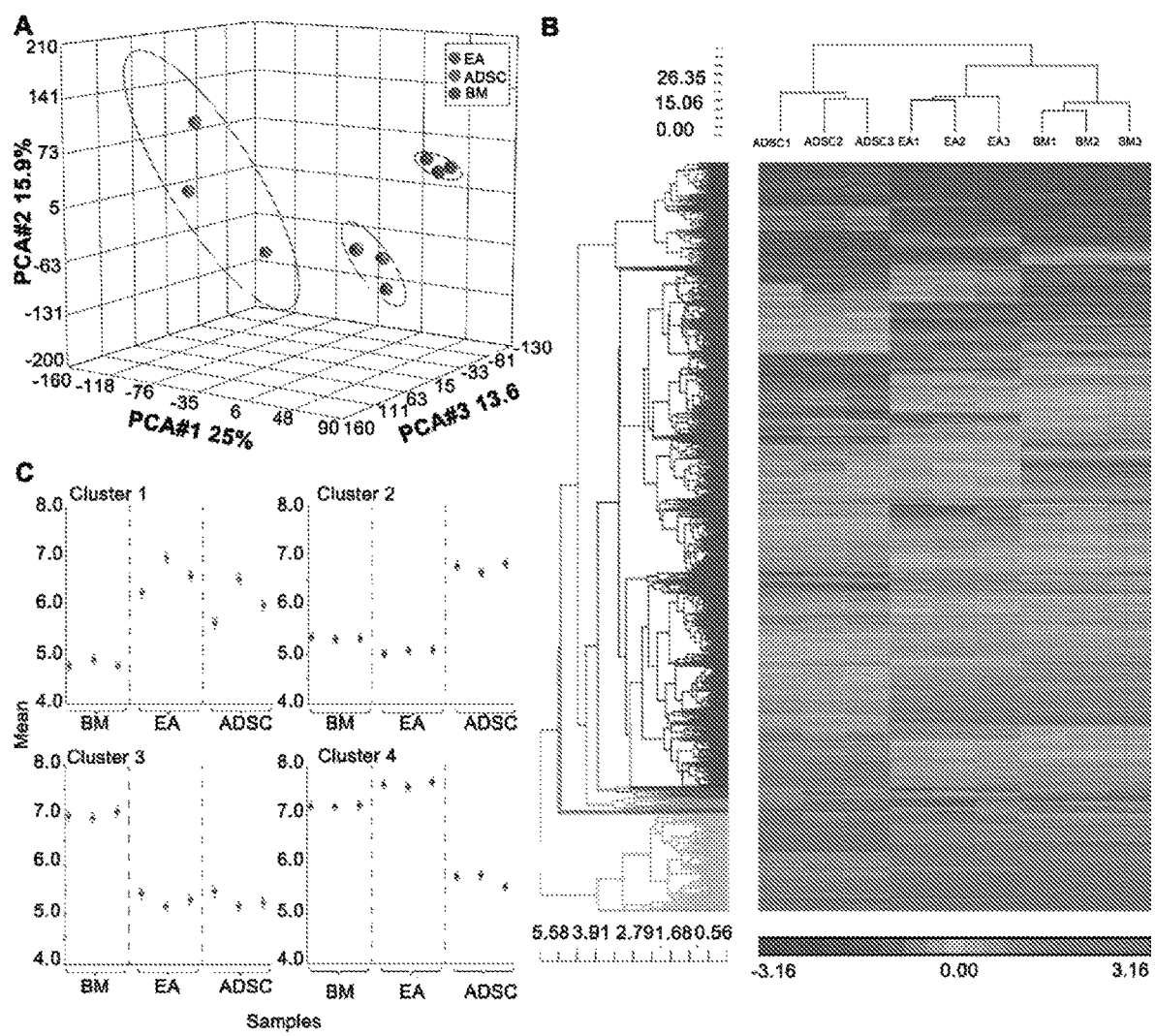
FIG. 2A-2C are graphs illustrating EA-mobilized cells showing a distinct origin from bone marrow-derived and adipose-derived equine MSCs. EA-mobilized cells (EA 1-EA 3) were compared to equine MSCs from bone marrow origin (BM1-BM3) and adipose-derived stem cells (ADSC1-ADSC3).

In contrast and not unexpected, AD-MSCs displayed highly increased expression of genes related to cholesterol, fatty acids and in general lipid metabolism, inflammatory response and redox homeostasis (FIG. 2C, Cluster 2), while BM-MSCs demonstrated increased expression of genes involved in inflammatory responses (acute phase, cytokine signaling), cell motility, and response to hormones and growth factors (FIG. 2C, Cluster 3).

Figure 10:
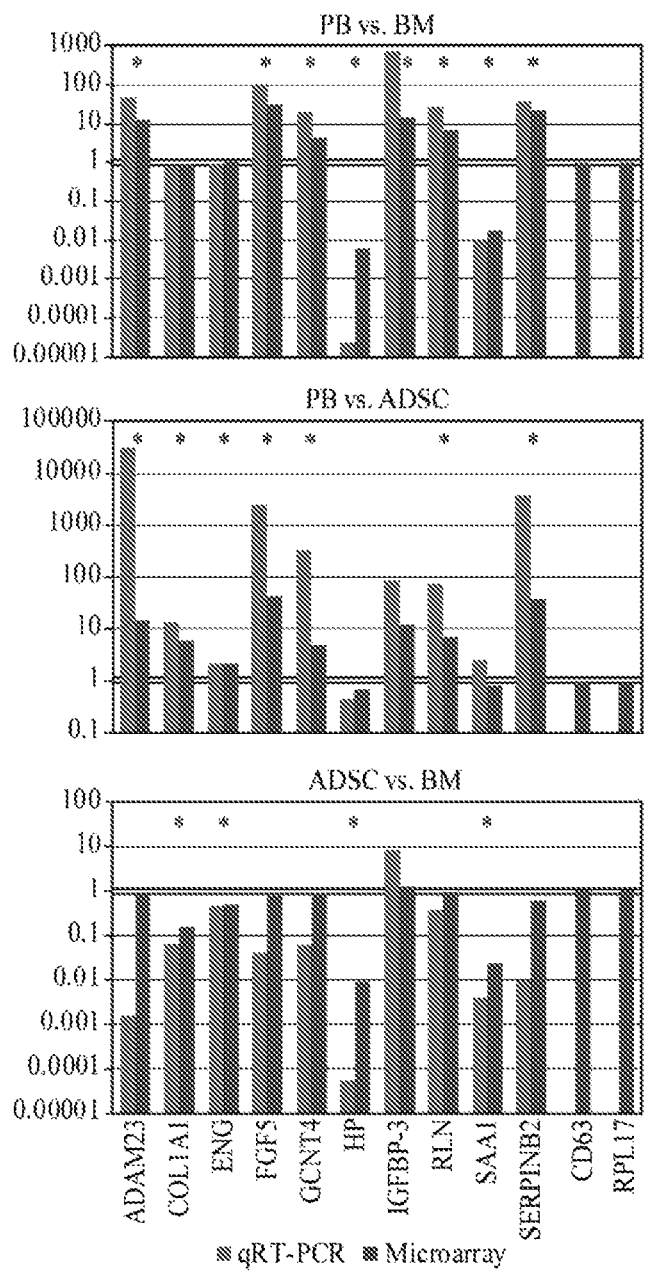
FIG. 10 are bar graphs illustrating qRT-PCR validation of select genes. A different representation of the same data as in FIG. 9, showing respective fold-changes. For each gene (X-axis), the following ratios were calculated, using all three samples per each group (Y axis): peripheral blood-derived cells vs. bone marrow-derived cells (PB vs. BM); peripheral blood-derived cells vs. adipose tissue-derived cells (PB vs. ADSC); adipose tissue-derived cells vs. bone marrow-derived cells (ADSC vs. BM). The ratios were represented for the two control genes calculated from microarray data (CD63 and RPL17) to show their constancy across samples. In all three panels, the double line marks a ratio of 1 (no change). *p<0.05 (ANOVA). Red: qRT-PCR data; blue: microarray data.

Several of the mentioned genes (ADAM23, COL1A1, ENG, FGF5, GCNT4, HP, IGFBP-3, RLN, SAA1, SER-PINB2, RPL17, CD63, NDUFA7) were further validated by real-time PCR (qRT-PCR) and showed similar differential gene expression patterns (FIGS. 9, 10), thus confirming the gene microarray results.

Figure 11:
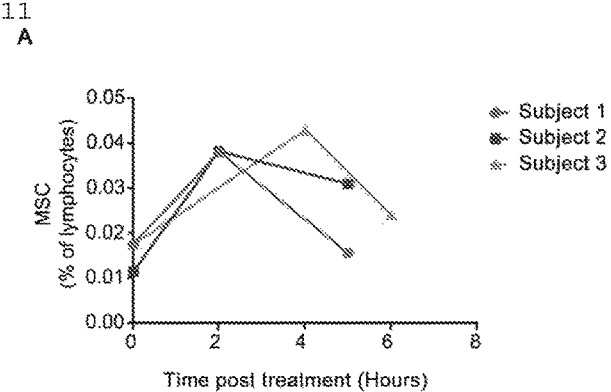
FIGS. 11A, 11B and 11C—pertain to a graph and photographs of release of MSCs in humans post EA treatment.
Figure 11:
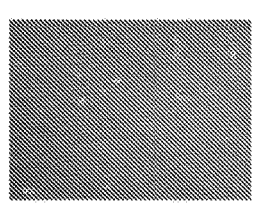
Figure 11C:
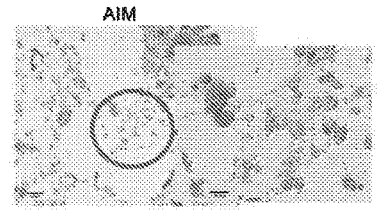
Figure 11C:
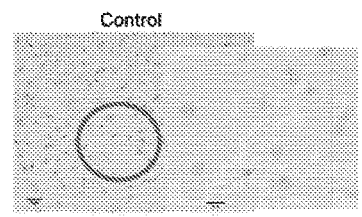

Example 7: EA Stimulation Induces an Increase in Circulating MSCs Across Species In order to explore whether the results observed in horses were reproducible in other species, we performed EA in humans using equivalent points to those used in horses. Peripheral blood cells before and following 16 minutes of EA were assessed by flow cytometry. A 300% increase in the percentage of MSCs ($CD44^+CD34^-$ $AC133^-$ $CD71^+$ $CD184^+CD105^+$ cells) was observed at 2 hours post EA compared to baseline (FIG. 3A, FIG. 3B) with a fall at later time points (FIG. 11).

Figure 3:
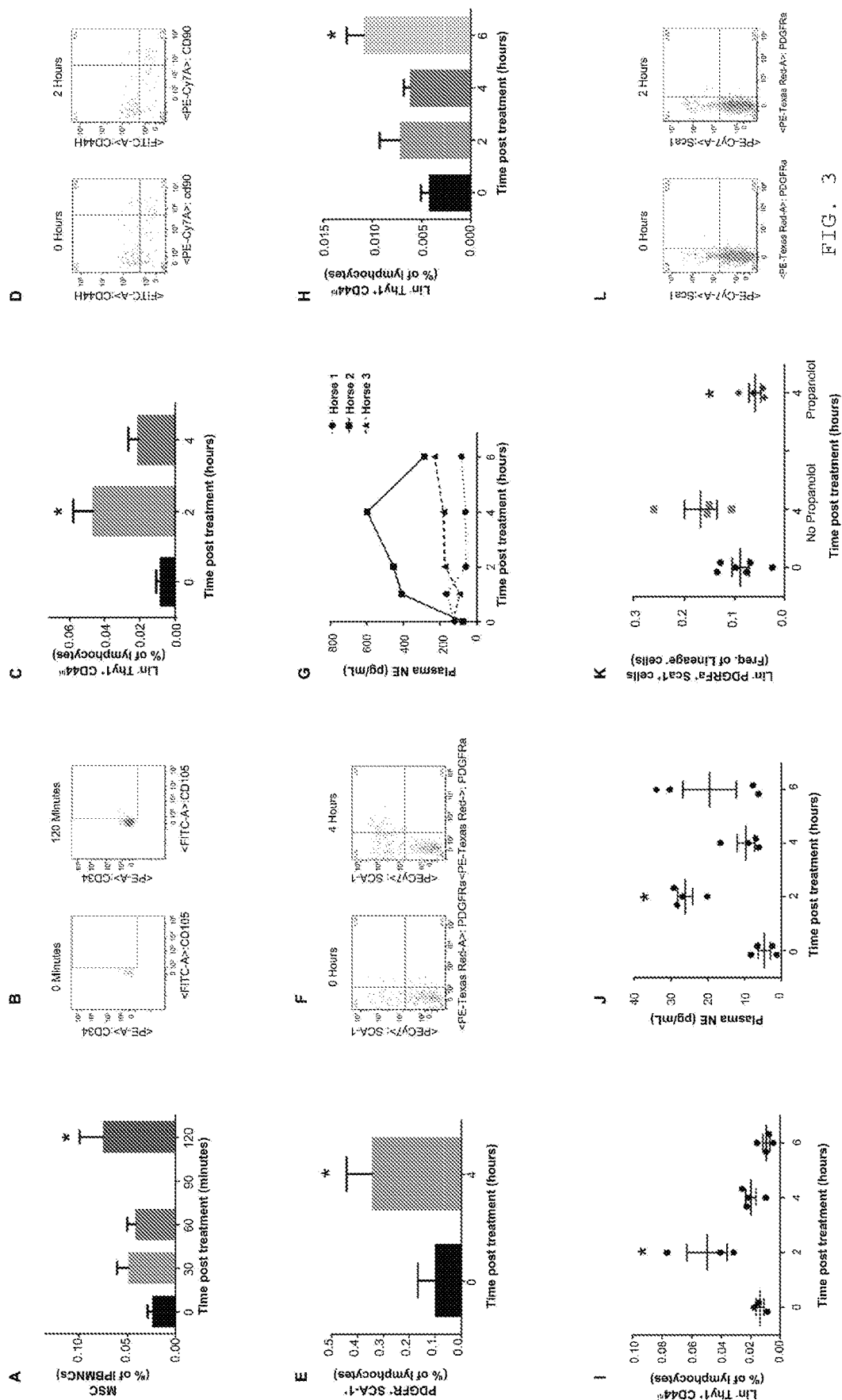
FIG. 3A-3L are graphs illustrating MSC increase in peripheral circulation of humans, rats and mice post acupuncture treatment.

To confirm these observations in additional species, we examined rats and mice. Using species-equivalent acu-points, a 313% increase in rat MSC (Lin– $CD90^+CD44^{hi}$ cells) was detected in the blood of EA-treated rats at 2 hours post EA compared to baseline (FIG. 3C, FIG. 3D). Similarly, a significant increase of MSCs was observed in the circulation of mice after EA (FIG. 3E, FIG. 3F). Overall, these data suggest that the mobilization of MSCs into circulation with EA is similar across the four different species.

Example 8: EA of Immune Points Results in Increased Norepinephrine Levels in the Blood Release of hematopoietic stem cells from the bone marrow is governed by post ganglionic sympathetic nerves.[14,15] To determine whether MSCs were similarly regulated by the sympathetic nervous system (SNS), the concentration of norepinephrine (NE) was measured in equine plasma before and following EA at immune points. EA resulted in an increase in plasma NE levels with the maximum level occurring at 4 hours post treatment (FIG. 3G). Importantly, there was no noticeable change in the levels of plasma NE concentration following stimulation at sham points, supporting the specificity of the response for immune points.

Exogenous administration of epinephrine by intra peritoneal (IP) injection in rats resulted in a similar increase of rat MSCs (Lin– $CD90^+CD44^{hi}$ cells) into the circulation (FIG. 3H) but at 6 hours, rather than 2 hours. IP injections of dopamine in rats (FIG. 3I) increased circulating MSCs at 2 hours with a peak in plasma NE concentration at 2 hours post administration (FIG. 3J), similar to what has been previously seen following IP administration of dopamine in mice.[16] To determine the selectivity of this response, mice were pretreated with the β adrenergic blocker, propranolol for 24 hours prior to EA and mobilization of MSCs was prevented ($p<0.01$) (FIG. 3K, FIG. 3L).

Example 9: Acupuncture Induces Activation of Hypothalamic Regions of the Brain in Rats The cumulative observations thus far would suggest that the SNS plays a role in mobilization of MSCs into peripheral blood. To examine the potential contribution of CNS activity in this, BOLD fMRI of rats undergoing EA was performed. Connectivity was derived from 4 time points: baseline, 0-8 min during EA, 9-22 min during EA, and immediately post-EA. The hypothalamus was chosen since it plays a critical role as a primary homeostatic center in the brain. This structure contains neurons with important projections to other limbic sites and sympathetic nuclei directly communicating with the periphery. Seed regions included the anterior, posterior, and lateral hypothalamus. A significant increase in connectivity during EA stimulation (FIG. 4A) was observed compared to baseline and the post-EA period. Thus acupuncture stimulation produces changes in the strength of functional connectivity within the hypothalamus and between the hypothalamus and adjacent brain regions such as the amygdala. Because the early onset of this central effect precedes the measured mobilization of MSC (FIG. 4A), it is proposed that the acupuncture-induced connectivity changes may contribute to their subsequent release.

Figure 4:
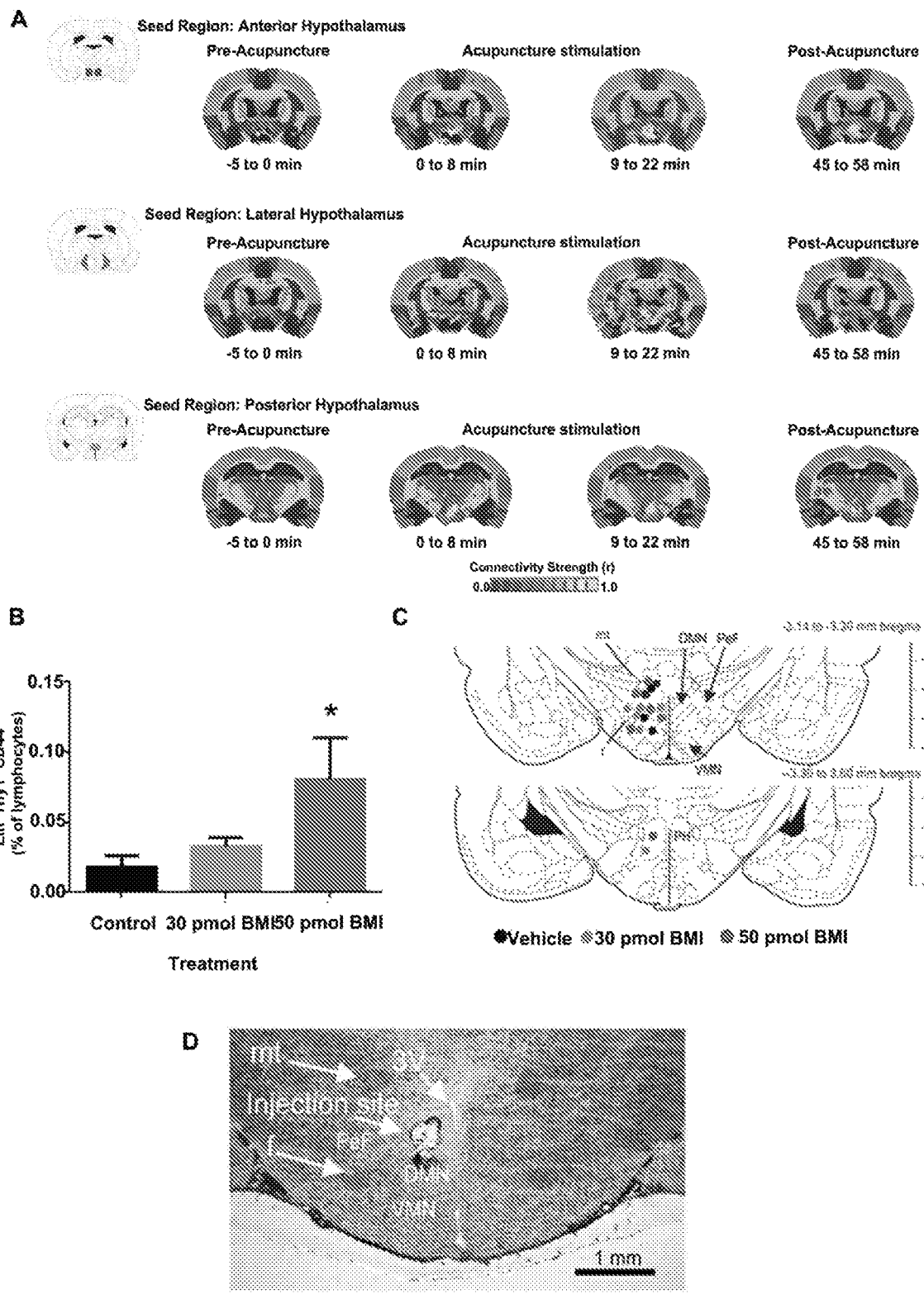
FIG. 4A-4D are photographs showing pharmacologically disinhibiting dorsomedial regions of the tuberal hypothalamus of rats and mobilized circulating MSCs.

Example 10: Pharmacological Disinhibition of the Dorsomedial Regions of the Tuberal Hypothalamus Mobilizes MSC Release into Circulation Stereotaxically disinhibiting the dorsomedial regions of the tuberal hypothalamus of rats with the GABAA receptor antagonist bicuculline methiodide (BMI) (30 pmol) did not alter the total number of cells in the blood ($F(2,14)=0.9$, $p=0.412$), but at the highest dose (50 pmol) did increase the percentage of MSCs (Lin– $CD90^+CD44^{hi}$ cells) ($F(2,14)=6.7$, $p=0.027$) at 4 hours post injection (FIG. 4B). Histological verification of injections sites is indicated in the illustration shown in (FIG. 4C). The exact location of all injections sites are shown on coronal sections from a Standard Stereotaxic Atlas of the Rat Brain,[17] and (FIG. 4D) photomicrograph shows a representative injection site from one rat.

Figure 5:
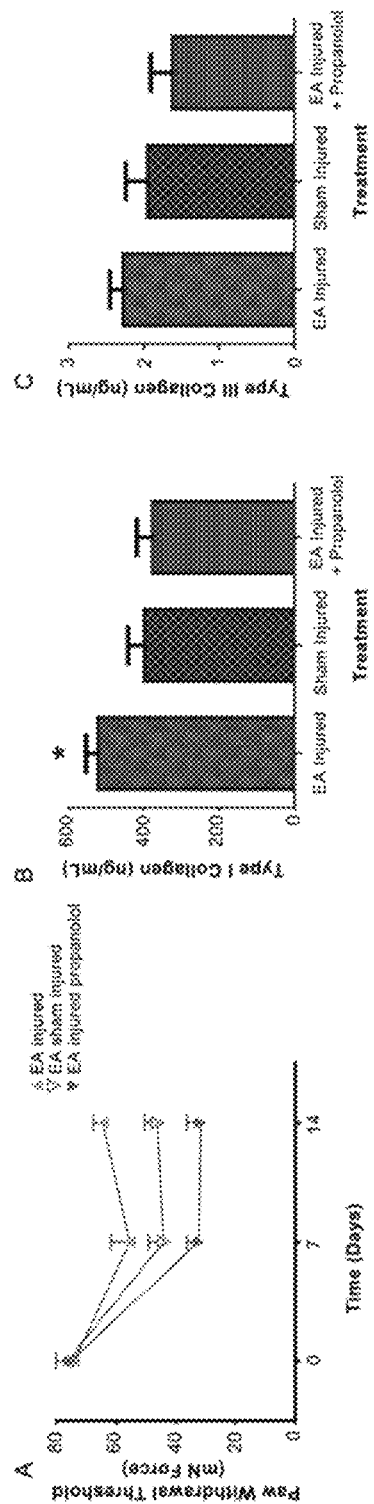
FIG. 5 C pertains to evaluation type III collagen.
Figure 6:
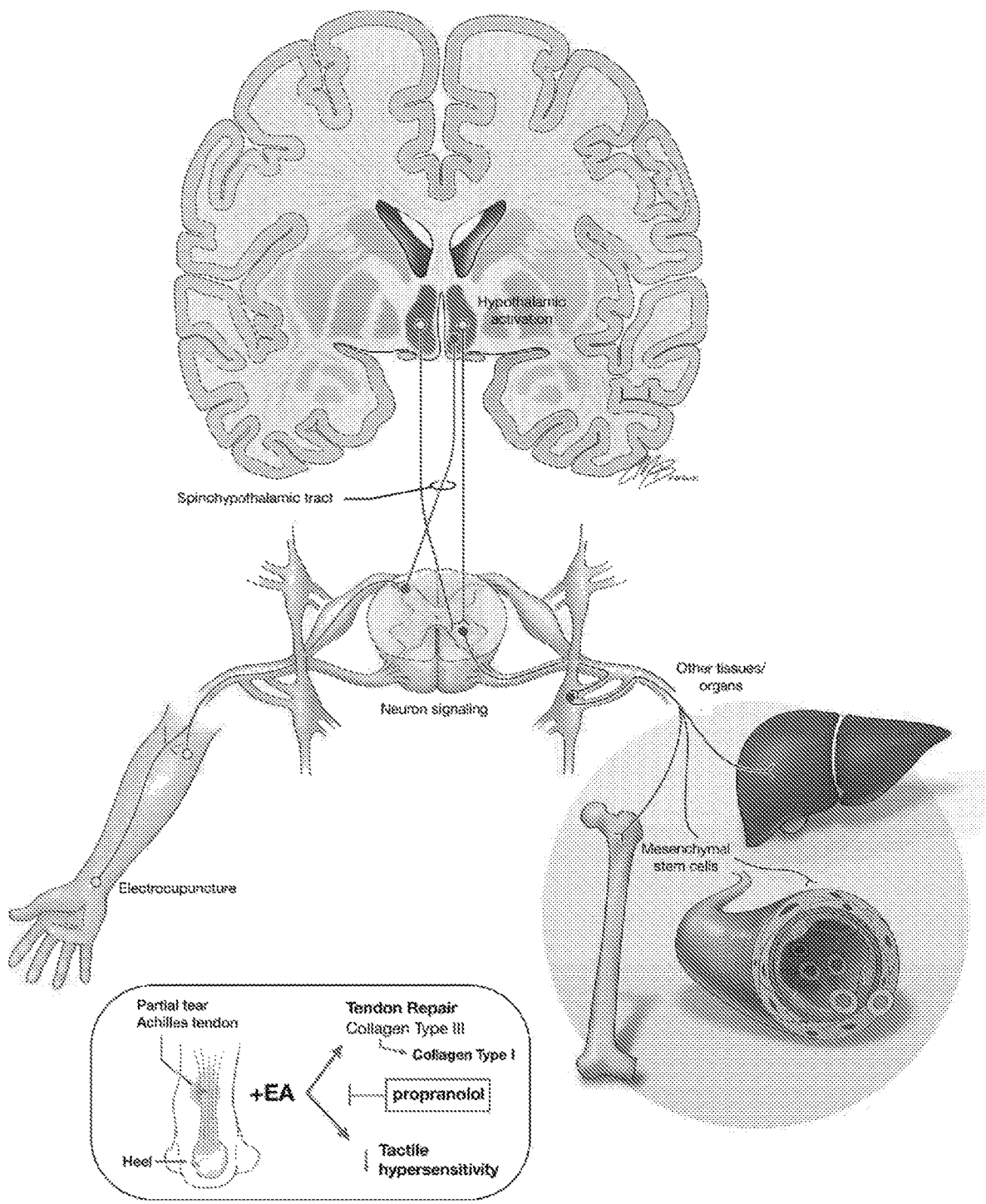
FIG. 6 is a representation showing EA mobilizes MSCs through hypothalamic activation of the sympathetic system. EA administration promotes a localized signal to access the hypothalamus via the spinohypothalamic tract leading to stimulation of the hypothalamus and subsequent sympathetic signaling to the peripheral organs to mobilize MSC from their tissue niches into the bloodstream.

Example 11: Rats Undergoing EA at Immune Points Demonstrate Reduces Mechanical Hyperalgesia and Enhanced Tissue Remodeling Following Tendon Rupture Chronic and acute tendon injuries are common and result in considerable pain and disability. MSCs may serve to suppress some aspects of inflammatory pain behavior. To address the possible functional effect of EA mobilization of MSCs on nociceptive modulation associated with partial tendon rupture, the contribution of an EA treatment paradigm was analyzed on injury-induced hyperalgesia in rats. Using sham EA applied to non-immune acupoints, nociceptive behavior elicited by von Frey mechanical stimulation did not change over the time course in the hind paw ipsilateral to the injury (FIG. 5A). In contrast, mechanical hyperalgesia was considerably decreased bilaterally in rodents subjected to the combination of tendon rupture and EA application at immune points, every other day for up to 14 days.

It was next explored whether the EA-mobilized MSCs could enhance tendon repair following experimentally-induced partial rupture. At the early stage of tendon repair, the granulation tissues mainly synthesize type III collagen. At later stages, intrinsic fibroblasts produce type I collagen, whose fibers are orientated more longitudinally to replace type III collagen. EA significantly enhanced type I collagen in the injured tendon by 14 days compared with the sham-treated tendons (FIG. 5B). Taken together, EA enhances the transformation of thinner and immature type III collagen fibers into mature type I collagen fibers in the injured tendon thereby supporting a better quality of regeneration and tissue reorganization.

REFERENCES

All references cited herein are hereby incorporated by reference in their entirety.
1. Skarda, R. T., Tejwani, G. A. & Muir, W. W., 3rd. Cutaneous analgesia, hemodynamic and respiratory effects, and beta-endorphin concentration in spinal fluid and plasma of horses after acupuncture and electroacupuncture. *American journal of veterinary research* 63, 1435-1442 (2002).
2. Steiss, J. E., White, N. A. & Bowen, J. M. Electroacupuncture in the treatment of chronic lameness in horses and ponies: a controlled clinical trial. *Canadian journal of veterinary research=Revue canadienne de recherche veterinaire* 53, 239-243 (1989).
3. Zijlstra, F. J., van den Berg-de Lange, I., Huygen, F. J. & Klein, J. Anti-inflammatory actions of acupuncture. *Mediators of inflammation* 12, 59-69 (2003).
4. Xie, H., Colahan, P. & Ott, E. A. Evaluation of electroacupuncture treatment of horses with signs of chronic thoracolumbar pain. *Journal of the American Veterinary Medical Association* 227, 281-286 (2005).
5. McCormick, W. H. Traditional Chinese channel diagnosis myosfascial pain syndrome and metacarpophalangeal joint trauma in the horse. *Journal of Equine Veterinary Science* 16, 562-567 (1996).
6. von Schweinitz, D. Thermographic evidence for the effectiveness of acupuncture in equine neuromuscular disease. *Acupuncture in Medicine*, 14-17 (1998).
7. Rogers, P. A., Schoen, A. M. & Limehouse, J. Acupuncture for immune-mediated disorders. Literature review and clinical applications. *Problems in veterinary medicine* 4, 162-193 (1992).
8. Zeng-bin Ma, Y.-y. Z., Liang-xiao Ma, Nan-nan Guo, Chun Li, Yan-ping Wang, Kai Cheng, Huan Yang, Wanning Liu, Kim Leo Wi, Jiang Zhu. Clinical Studies on the Indications of 33 Acupoints. *Medical Acupuncture* 20, 269-275 (2008).
9. Urano, K. & Ogasawara, S. A fundamental study on acupuncture points phenomena of dog body. *The Kitasato archives of experimental medicine* 51, 95-109 (1978).
10. Gunn, C. C., Ditchburn, F. G., King, M. H. & Renwick, G. J. Acupuncture loci: a proposal for their classification according to their relationship to known neural structures. *The American journal of Chinese medicine* 4, 183-195 (1976).
11. Toyama, P. M. & Nishizawa, M. The physiological basis of acupuncture therapy. *Journal of the National Medical Association* 64, 397-402 (1972).
12. Richardson, M. R., et al. Angiopoietin-like protein 2 regulates endothelial colony forming cell vasculogenesis. *Angiogenesis* 17, 675-683 (2014).
13. Diez, H., et al. Hypoxia-mediated activation of Dll4-Notch-Hey2 signaling in endothelial progenitor cells and adoption of arterial cell fate. *Experimental cell research* 313, 1-9 (2007).
14. Mendez-Ferrer, S., Battista, M. & Frenette, P. S. Cooperation of beta(2)- and beta(3)-adrenergic receptors in hematopoietic progenitor cell mobilization. *Annals of the New York Academy of Sciences* 1192, 139-144 (2010).
15. Katayama, Y., et al. Signals from the sympathetic nervous system regulate hematopoietic stem cell egress from bone marrow. *Cell* 124, 407-421 (2006).
16. Torres-Rosas, R., et al. Dopamine mediates vagal modulation of the immune system by electroacupuncture. *Nature medicine* 20, 291-295 (2014).
17. Paxinos, G. a. W., Charles. *The Rat Brain in Stereotaxic Coordinates*, (Academic Press, 2007).
18. Maxson, S., Lopez, E. A., Yoo, D., Danilkovitch-Miagkova, A. & Leroux, M. A. Concise review: role of mesenchymal stem cells in wound repair. *Stem cells translational medicine* 1, 142-149 (2012).
19. Bull, N. D. & Martin, K. R. Concise review: toward stem cell-based therapies for retinal neurodegenerative diseases. *Stem cells* 29, 1170-1175 (2011).
20. Wu, Y., Zhao, R. C. & Tredget, E. E. Concise review: bone marrow-derived stem/progenitor cells in cutaneous repair and regeneration. *Stem cells* 28, 905-915 (2010).
21. Deng, J., et al. Bone marrow mesenchymal stem cells can be mobilized into peripheral blood by G-CSF in vivo and integrate into traumatically injured cerebral tissue. *Neurological sciences: official journal of the Italian Neurological Society and of the Italian Society of Clinical Neurophysiology* 32, 641-651 (2011).
22. Hong, H. S., et al. A new role of substance P as an injury-inducible messenger for mobilization of CD29(+) stromal-like cells. *Nature medicine* 15, 425-435 (2009).
23. Krampera, M., Pizzolo, G., Aprili, G. & Franchini, M. Mesenchymal stem cells for bone, cartilage, tendon and skeletal muscle repair. *Bone* 39, 678-683 (2006).
24. Tyndall, A., et al. Immunomodulatory properties of mesenchymal stem cells: a review based on an interdisciplinary meeting held at the Kennedy Institute of Rheumatology Division, London, UK, 31 Oct. 2005. *Arthritis research & therapy* 9, 301 (2007).
25. Steinert, A. F., Rackwitz, L., Gilbert, F., Noth, U. & Tuan, R. S. Concise review: the clinical application of mesenchymal stem cells for musculoskeletal regeneration: current status and perspectives. *Stem cells translational medicine* 1, 237-247 (2012).
26. Duijvestein, M., et al. Autologous bone marrow-derived mesenchymal stromal cell treatment for refractory luminal Crohn's disease: results of a phase I study. *Gut* 59, 1662-1669 (2010).
27. Le Blanc, K., et al. Mesenchymal stem cells for treatment of steroid-resistant, severe, acute graft-versus-host disease: a phase II study. *Lancet* 371, 1579-1586 (2008).
28. Tan, J., et al. Induction therapy with autologous mesenchymal stem cells in living-related kidney transplants: a randomized controlled trial. *JAMA: the journal of the American Medical Association* 307, 1169-1177 (2012).
29. Ciccocioppo, R., et al. Autologous bone marrow-derived mesenchymal stromal cells in the treatment of fistulising Crohn's disease. *Gut* 60, 788-798 (2011).
30. Hare, J. M., et al. Comparison of allogeneic vs autologous bone marrow-derived mesenchymal stem cells delivered by transendocardial injection in patients with ischemic cardiomyopathy: the POSEIDON randomized trial. *JAMA: the journal of the American Medical Association* 308, 2369-2379 (2012).
31. Goldstein, D. S., McCarty, R., Polinsky, R. J. & Kopin, I. J. Relationship between plasma norepinephrine and sympathetic neural activity. *Hypertension* 5, 552-559 (1983).
32. Wible, J. H., Jr., DiMicco, J. A. & Luft, F. C. Hypothalamic GABA and sympathetic regulation in spontaneously hypertensive rats. *Hypertension* 14, 623-628 (1989).

33. Wilent, W. B., et al. Induction of panic attack by stimulation of the ventromedial hypothalamus. *Journal of neurosurgery* 112, 1295-1298 (2010).
34. Kremer, H. P. The hypothalamic lateral tuberal nucleus: normal anatomy and changes in neurological diseases. *Progress in brain research* 93, 249-261 (1992).
35. Shepherd, A. J., Downing, J. E. & Miyan, J. A. Without nerves, immunology remains incomplete—in vivo veritas. *Immunology* 116, 145-163 (2005).
36. Mendez-Ferrer, S., Lucas, D., Battista, M. & Frenette, P. S. Haematopoietic stem cell release is regulated by circadian oscillations. *Nature* 452, 442-447 (2008).
37. Lucas, D., et al. Norepinephrine reuptake inhibition promotes mobilization in mice: potential impact to rescue low stem cell yields. *Blood* 119, 3962-3965 (2012).
38. Kumar, S. & Ponnazhagan, S. Mobilization of bone marrow mesenchymal stem cells in vivo augments bone healing in a mouse model of segmental bone defect. *Bone* 50, 1012-1018 (2012).
39. Kassis, I., et al. Isolation of mesenchymal stem cells from G-CSF-mobilized human peripheral blood using fibrin microbeads. *Bone marrow transplantation* 37, 967-976 (2006).
40. Broxmeyer, H. E., et al. Rapid mobilization of murine and human hematopoietic stem and progenitor cells with AMD3100, a CXCR4 antagonist. *The Journal of experimental medicine* 201, 1307-1318 (2005).
41. Kawada, H., et al. Nonhematopoietic mesenchymal stem cells can be mobilized and differentiate into cardiomyocytes after myocardial infarction. *Blood* 104, 3581-3587 (2004).
42. Zhang, Y., et al. Electroacupuncture inhibition of hyperalgesia in an inflammatory pain rat model: involvement of distinct spinal serotonin and norepinephrine receptor subtypes. *British journal of anaesthesia* 109, 245-252 (2012).
43. Kim, J. H., Kim, H. Y., Chung, K. & Chung, J. M. Electroacupuncture reduces the evoked responses of the spinal dorsal horn neurons in ankle-sprained rats. *Journal of neurophysiology* 105, 2050-2057 (2011).
44. Koo, S. T., Lim, K. S., Chung, K., Ju, H. & Chung, J. M. Electroacupuncture-induced analgesia in a rat model of ankle sprain pain is mediated by spinal alpha-adrenoceptors. *Pain* 135, 11-19 (2008).
45. Koo, S. T., Park, Y. I., Lim, K. S., Chung, K. & Chung, J. M. Acupuncture analgesia in a new rat model of ankle sprain pain. *Pain* 99, 423-431 (2002).
46. Silva, J. R., Silva, M. L. & Prado, W. A. Analgesia induced by 2- or 100-Hz electroacupuncture in the rat tail-flick test depends on the activation of different descending pain inhibitory mechanisms. *The journal of pain: official journal of the American Pain Society* 12, 51-60 (2011).
47. Newman, R. E., Yoo, D., LeRoux, M. A. & Danilkovitch-Miagkova, A. Treatment of inflammatory diseases with mesenchymal stem cells. *Inflammation & allergy drug targets* 8, 110-123 (2009).
48. Chamberlain, G., Fox, J., Ashton, B. & Middleton, J. Concise review: mesenchymal stem cells: their phenotype, differentiation capacity, immunological features, and potential for homing. *Stem cells* 25, 2739-2749 (2007).
49. Chen, X. M., Xu, J., Song, J. G., Zheng, B. J. & Wang, X. R. Electroacupuncture inhibits excessive interferon-gamma evoked up-regulation of P2X4 receptor in spinal microglia in a CCI rat model for neuropathic pain. *British journal of anaesthesia* 114, 150-157 (2015).
50. Wang, Y., et al. CXCL10 controls inflammatory pain via opioid peptide-containing macrophages in electroacupuncture. *PloS one* 9, e94696 (2014).
51. Inoue, M., et al. The effect of electroacupuncture on tendon repair in a rat Achilles tendon rupture model. *Acupuncture in medicine: journal of the British Medical Acupuncture Society* 33, 58-64 (2015).
52. Ringden, O., et al. Mesenchymal stem cells for treatment of therapy-resistant graft-versus-host disease. *Transplantation* 81, 1390-1397 (2006).
53. Le Blanc, K., et al. Treatment of severe acute graft-versus-host disease with third party haploidentical mesenchymal stem cells. *Lancet* 363, 1439-1441 (2004).
54. Meng, H., Zhai, X., Hao, J. D. & Wang, H. C. [Intervention of electroacupuncture for patients with impaired glucose tolerance]. *Zhongguo Zhen Jiu* 31, 971-973.
55. Min, Y., Seo, J. H., Kwon, Y. B. & Lee, M. H. Effect of the position of immobilization upon the tensile properties in injured achilles tendon of rat. *Annals of rehabilitation medicine* 37, 1-9 (2013).
56. Martin-Ramirez, J., Hofman, M., van den Biggelaar, M., Hebbel, R. P. & Voorberg, J. Establishment of outgrowth endothelial cells from peripheral blood. *Nature protocols* 7, 1709-1715 (2012).
57. Ingram, D. A., et al. Vessel wall-derived endothelial cells rapidly proliferate because they contain a complete hierarchy of endothelial progenitor cells. *Blood* 105, 2783-2786 (2005).
58. Ingram, D. A., et al. Identification of a novel hierarchy of endothelial progenitor cells using human peripheral and umbilical cord blood. *Blood* 104, 2752-2760 (2004).
59. Ishihara, A., et al. Performance of a gravitational marrow separator, multidirectional bone marrow aspiration needle, and repeated bone marrow collections on the production of concentrated bone marrow and separation of mesenchymal stem cells in horses. *American journal of veterinary research* 74, 854-863 (2013).
60. Cai, L., et al. IFATS collection: Human adipose tissue-derived stem cells induce angiogenesis and nerve sprouting following myocardial infarction, in conjunction with potent preservation of cardiac function. *Stem cells* 27, 230-237 (2009).
61. Bailey, J. L., et al. Collagen oligomers modulate physical and biological properties of three-dimensional self-assembled matrices. *Biopolymers* 95, 77-93 (2011).
62. Gavrilin, M. A., et al. Internalization and phagosome escape required for *Francisella* to induce human monocyte IL-1beta processing and release. *Proceedings of the National Academy of Sciences of the United States of America* 103, 141-146 (2006).
63. Mund, J. A., et al. Human proangiogenic circulating hematopoietic stem and progenitor cells promote tumor growth in an orthotopic melanoma xenograft model. *Angiogenesis* 16, 953-962 (2013).
64. Estes, M. L., et al. Application of polychromatic flow cytometry to identify novel subsets of circulating cells with angiogenic potential. *Cytometry. Part A: the journal of the International Society for Analytical Cytology* 77, 831-839 (2010).
65. Estes, M. L., Mund, J. A., Ingram, D. A. & Case, J. Identification of endothelial cells and progenitor cell subsets in human peripheral blood. *Current protocols in cytometry/editorial board, J. Paul Robinson, managing editor . . . [et al.]* Chapter 9, Unit 9 33 31-11 (2010).
66. Martins, A. A., Paiva, A., Morgado, J. M., Gomes, A. & Pais, M. L. Quantification and immunophenotypic characterization of bone marrow and umbilical cord blood mesenchymal stem cells by multicolor flow cytometry. *Transplantation proceedings* 41, 943-946 (2009).
67. Baumgarth, N. & Roederer, M. A practical approach to multicolor flow cytometry for immunophenotyping. *Journal of immunological methods* 243, 77-97 (2000).
68. Liang, Z., Li, T., King, J. & Zhang, N. Mapping thalamocortical networks in rat brain using resting-state functional connectivity. *NeuroImage* 83, 237-244 (2013).
69. Samuels, B. C., Zaretsky, D. V. & DiMicco, J. A. Dorsomedial hypothalamic sites where disinhibition evokes tachycardia correlate with location of raphe-projecting neurons. *American journal of physiology. Regulatory, integrative and comparative physiology* 287, R472-478 (2004).
70. Bhangoo, S. K., et al. CXCR4 chemokine receptor signaling mediates pain hypersensitivity in association with antiretroviral toxic neuropathy. *Brain, behavior, and immunity* 21, 581-591 (2007).
71. Ma, C., et al. Similar electrophysiological changes in axotomized and neighboring intact dorsal root ganglion neurons. *Journal of neurophysiology* 89, 1588-1602 (2003).

TABLE S1

Top significantly up-regulated genes in EA-mobilized MSC as compared to bone marrow-derived (BM) MSC and adipose-derived stem cells (ADSC).

| Gene Symbol* | Gene ID | Fold-Change (EA vs. BM) | p-value (EA vs. BM) | Fold-Change (EA vs. ADSC) | p-value (EA vs. ADSC) |
| --- | --- | --- | --- | --- | --- |
| FGF5 | 15070828 | 32.04 | 3.59E-06 | 41.00 | 2.39E-06 |
| PCSK1 | 14983691 | 28.53 | 2.44E-04 | 15.74 | 7.03E-04 |
| SERPINB2 | 15116836 | 22.70 | 4.89E-04 | 36.16 | 2.29E-04 |
| SLITRK4 | 15133650 | 19.17 | 5.77E-06 | 16.31 | 8.02E-06 |
| IGFBP-3 | 15080887 | 15.28 | 6.19E-04 | 12.20 | 9.77E-04 |
| CG | 14956430 | 15.25 | 3.97E-03 | 2.47 | 1.83E-01 |
| SERPINB10 | 15118865 | 14.89 | 3.14E-04 | 19.27 | 1.90E-04 |
| ANKRD1 | 14934054 | 12.90 | 1.14E-02 | 58.93 | 1.23E-03 |
| ADAM23 | 15008388 | 12.44 | 1.08E-04 | 14.22 | 8.04E-05 |
| CDA | 15023541 | 11.91 | 1.22E-03 | 10.33 | 1.65E-03 |
| IL11 | 14955834 | 11.89 | 1.67E-04 | 14.12 | 1.15E-04 |
| DES | 15094232 | 11.70 | 1.27E-04 | 17.90 | 5.12E-05 |
| GPR87 | 15002289 | 11.16 | 2.20E-03 | 11.18 | 2.20E-03 |
| ARHGDIB | 15100700 | 10.74 | 2.85E-03 | 31.43 | 4.10E-04 |
| SHOX2 | 15013614 | 9.79 | 2.24E-05 | 2.40 | 4.02E-03 |
| ABCB1 | 15081264 | 9.00 | 1.85E-04 | 5.35 | 8.03E-04 |
| CDK1 | 14934268 | 8.79 | 4.14E-04 | 1.52 | 2.25E-01 |
| AURKB | 14968625 | 8.36 | 4.69E-03 | 1.79 | 2.75E-01 |
| CEP55 | 14942597 | 8.16 | 1.09E-02 | -1.05 | 9.35E-01 |
| BDNF | 15113171 | 7.97 | 1.46E-04 | 13.68 | 3.93E-05 |
| SERPINB7 | 15116842 | 7.70 | 4.25E-04 | 7.33 | 4.86E-04 |
| NTM | 15105569 | 7.48 | 1.89E-03 | 7.77 | 1.72E-03 |
| ALCAM | 15015272 | 7.45 | 1.38E-04 | 4.92 | 4.90E-04 |
| CDCA3 | 15100085 | 7.01 | 4.32E-03 | 1.68 | 2.80E-01 |
| PROCR | 15087557 | 6.97 | 7.63E-04 | 1.40 | 3.23E-01 |
| NDC80 | 15115854 | 6.93 | 3.24E-03 | 1.42 | 4.25E-01 |
| CCNB2 | 14946493 | 6.83 | 1.65E-03 | 1.12 | 7.61E-01 |
| CCNA2 | 15020878 | 6.81 | 6.56E-03 | 1.35 | 5.47E-01 |
| RLN | 15043398 | 6.70 | 5.69E-03 | 6.81 | 5.47E-03 |
| RRM2 | 14994507 | 6.64 | 1.50E-03 | 2.64 | 3.03E-02 |
| UBE2C | 15038211 | 6.64 | 2.88E-03 | 1.33 | 4.95E-01 |
| TNN | 15084476 | 6.52 | 4.43E-04 | 10.77 | 1.19E-04 |
| TPX2 | 15037163 | 6.45 | 1.26E-02 | 1.62 | 3.98E-01 |
| FAM54A | 14957724 | 6.42 | 8.04E-03 | 1.13 | 8.04E-01 |
| KIAA0101 | 14937533 | 6.41 | 2.10E-03 | 1.44 | 3.47E-01 |
| LECT2 | 14982913 | 6.37 | 1.11E-05 | 4.26 | 4.55E-05 |
| HELLS | 14942491 | 6.09 | 9.28E-03 | 1.50 | 4.32E-01 |
| AMIGO2 | 15101513 | 6.08 | 4.88E-03 | 2.41 | 7.93E-02 |
| BUB1B | 14947475 | 6.07 | 1.51E-03 | -1.06 | 8.75E-01 |
| NUSAP1 | 14947311 | 6.02 | 3.15E-03 | 1.52 | 3.08E-01 |
| CENPN | 15065467 | 6.01 | 3.41E-03 | 1.16 | 7.06E-01 |
| EVI2A | 14961882 | 6.00 | 1.20E-02 | 1.83 | 2.78E-01 |
| TOP2A | 14960493 | 5.93 | 4.36E-03 | 1.32 | 5.09E-01 |
| FAIM2 | 15101902 | 5.76 | 2.34E-02 | 4.80 | 3.53E-02 |
| FABP6 | 14984980 | 5.75 | 2.25E-03 | 9.81 | 5.62E-04 |
| SGCG | 15002551 | 5.70 | 8.73E-02 | -2.53 | 3.19E-01 |
| HMMR | 14984908 | 5.65 | 1.35E-02 | 1.19 | 7.46E-01 |
| TTK | 14952269 | 5.62 | 7.83E-03 | 1.10 | 8.42E-01 |
| ASPM | 15074537 | 5.54 | 1.52E-02 | -1.29 | 6.38E-01 |
| SHCBP1 | 15068532 | 5.52 | 2.40E-03 | 1.50 | 2.82E-01 |
| NUF2 | 15090368 | 5.45 | 1.96E-03 | -1.03 | 9.35E-01 |
| ASAP2 | 14994578 | 5.44 | 1.07E-04 | 5.12 | 1.30E-04 |
| CENPI | 15129074 | 5.37 | 7.46E-03 | 1.12 | 8.05E-01 |
| ANLN | 15078331 | 5.15 | 2.34E-02 | 1.98 | 2.56E-01 |
| CRLF1 | 15034799 | 6.06 | 3.88E-04 | 10.62 | 4.71E-05 |
| CENPF | 15090061 | 5.05 | 9.23E-03 | 1.21 | 6.68E-01 |
| MIR221 | 15131506 | 5.03 | 1.42E-02 | 4.86 | 1.56E-02 |
| CDKN3 | 15044273 | 5.03 | 1.78E-02 | 1.10 | 8.50E-01 |
| PHYHIPL | 14934261 | 4.89 | 5.17E-04 | 7.95 | 1.18E-04 |
| DSCC1 | 15124409 | 4.86 | 9.06E-03 | 2.55 | 6.59E-02 |
| DHFR | 14983935 | 4.82 | 9.34E-03 | 1.20 | 6.72E-01 |
| DIAPH3 | 15005311 | 4.75 | 6.51E-03 | -1.05 | 8.94E-01 |
| ENC1 | 14984171 | 4.70 | 8.46E-04 | 4.95 | 7.11E-04 |
| PCOLCE2 | 15002101 | 4.70 | 1.98E-03 | -1.93 | 6.89E-02 |
| HTR2A | 15003284 | 4.70 | 6.44E-04 | 8.94 | 9.50E-05 |
| DHRS9 | 15007088 | 4.63 | 3.62E-04 | 12.11 | 2.32E-05 |
| CDS1 | 15070754 | 4.59 | 2.13E-02 | 1.79 | 2.84E-01 |
| EXO1 | 15074033 | 4.57 | 1.44E-02 | 1.06 | 9.05E-01 |
| CENPE | 15065998 | 4.54 | 2.30E-02 | 1.42 | 5.11E-01 |
| CRISP3 | 15031939 | 4.53 | 2.98E-01 | 59.90 | 2.15E-02 |
| SKA1 | 15116483 | 4.53 | 1.69E-02 | 1.91 | 2.11E-01 |
| KIF20A | 14985856 | 4.50 | 1.11E-02 | 1.68 | 2.61E-01 |
| CDH2 | 15119779 | 4.50 | 1.21E-03 | 12.18 | 7.55E-05 |
| GPR37 | 15082606 | 4.48 | 7.40E-04 | 6.20 | 2.57E-04 |
| NCAPG | 15072200 | 4.43 | 4.09E-03 | 1.41 | 3.39E-01 |
| NCAPH | 14991781 | 4.40 | 8.63E-03 | 1.35 | 4.69E-01 |
| DLGAP5 | 15046735 | 4.35 | 2.71E-02 | 1.18 | 7.55E-01 |
| PTHLH | 15101059 | 4.35 | 6.64E-03 | 11.00 | 5.69E-04 |
| GCNT4 | 14934135 | 4.34 | 7.46E-05 | 4.73 | 5.38E-05 |
| CPE | 15025275 | 4.32 | 4.59E-03 | -2.16 | 5.98E-02 |
| IL18 | 15109651 | 4.29 | 3.61E-03 | 7.70 | 6.41E-04 |
| PDLIM1 | 14933875 | 4.27 | 7.43E-04 | 4.07 | 8.88E-04 |
| CDC6 | 14965791 | 4.26 | 1.07E-02 | 2.39 | 7.12E-02 |
| PRC1 | 14944797 | 4.25 | 1.03E-02 | 1.46 | 3.72E-01 |
| BAIAP2L1 | 14974621 | 4.21 | 6.41E-05 | 3.01 | 2.85E-04 |
| KIF23 | 14946062 | 4.14 | 8.66E-03 | 1.41 | 3.91E-01 |
| GNA14 | 15041605 | 4.12 | 2.14E-02 | 5.24 | 1.12E-02 |
| KIF11 | 14942647 | 4.10 | 2.94E-02 | 1.26 | 6.58E-01 |
| HAND2 | 15019992 | 4.09 | 8.22E-03 | 4.55 | 5.86E-03 |
| FBLN2 | 14994834 | 4.00 | 2.07E-06 | 3.11 | 6.65E-06 |

Only annotated, unique genes from the chip are presented

TABLE S2

Top canonical pathways identified by Ingenuity Pathways Analysis to be different between EA mobilized equine cells and equine BM derived Mesenchymal Stem Cells

| Ingenuity Canonical Pathways | −log (p-value) | Ratio | Molecules |
|---|---|---|---|
| Mitotic Roles of Polo-Like Kinase | 6.68E+00 | 1.67E−01 | KIF23, CDC25C, PLK4, CDC20, WEE1, PRC1, CCNB2, FBXO5, CDK1, CHEK2, KIF11 |
| Cell Cycle: G2/M DNA Damage Checkpoint Regulation | 5.94E+00 | 1.84E−01 | CDC25C, KAT2B, GADD45A, WEE1, TOP2A, CCNB2, AURKA, CDK1, CHEK2 |
| Cell Cycle Control of Chromosomal Replication | 5.81E+00 | 2.59E−01 | MCM5, MCM3, MCM6, CDC45, CDC6, CHEK2, MCM4 |
| ATM Signaling | 4.34E+00 | 1.36E−01 | CDC25C, SMC2, FANCD2, GADD45A, SMC1B, CCNB2, CDK1, CHEK2 |
| Acute Phase Response Signaling | 3.97E+00 | 7.69E−02 | FN1, C1S, SERPINF1, CP, C1R, ALB, IL36G, IL18, HP, APOA1, SAA1, MAPK3, OSMR |
| Hepatic Fibrosis/Hepatic Stellate Cell Activation | 3.86E+00 | 7.11E−02 | VCAM1, FN1, FGF2, IFNGR2, VEGFB, MMP13, IFNAR2, TGFBR2, IGF2, IGF1, CCL2, COL11A1, KLF12, PDGFD |
| Role of IL-17F in Allergic Inflammatory Airway Diseases | 3.39E+00 | 1.36E−01 | IGF1, CCL2, MARK3, MMP13, RPS6KA2, IL11 |
| Atherosclerosis Signaling | 3.37E+00 | 8.13E−02 | ALB, IL36G, IL18, VCAM1, APOA1, CCL2, CXCR4, MMP13, PDGFD, TNFRSF12A |
| Pyridoxal 5'-phosphate Salvage Pathway | 3.27E+00 | 1.09E−01 | PAK1, MAPK3, GRK5, TTK, NEK2, CDK1, ACVR2A |
| GADD45 Signaling | 3.14E+00 | 2.11E−01 | CCNE2, CCND2, GADD45A, CDK1 |
| Salvage Pathways of Pyrimidine Ribonucleotides | 2.90E+00 | 8.42E−02 | PAK1, MAPK3, GRK5, TTK, NEK2, CDA, CDK1, ACVR2A |
| FXR/RXR Activation | 2.67E+00 | 7.09E−02 | BAAT, ALB, IL36G, IL18, APoA1, FABP6, SAA1, SERPINF1, NR5A2 |
| Anti-proliferative Role of TOB in T Cell Signaling | 2.61E+00 | 1.54E−01 | TGFBR2, CCNA2, CCNE2, TOB1 |
| Role of Tissue Factor in Cancer | 2.50E+00 | 7.27E−02 | PAK1, MAPK3, ITGA6, PLAUR, MMP13, GNA14, RPS6KA2, FGF5 |
| Axonal Guidance Signaling | 2.40E+00 | 4.39E−02 | SEMA3E, TUBB4B, BDNF, CXCR4, VEGFB, MMP13, GNA14, FZD1, SLIT2, PAK1, ADAMTS6, ADAM12, IGF1, SDC2, MAPK3, ARHGEF6, ADAM23, TUBA1C, PDGFD |
| Mismatch Repair in Eukaryotes | 2.31E+00 | 1.88E−01 | RFC4, FEN1, EXO1 |
| HMGB1 Signaling | 2.27E+00 | 6.67E−02 | IL18, VCAM1, KAT2B, CCL2, MAPK3, IFNGR2, IL11, PLAT |
| Amyotrophic Lateral Sclerosis Signaling | 2.20E+00 | 7.14E−02 | PAK1, GRIK5, IGF1, GRID1, CAT, VEGFB, BIRC2 |
| p53 Signaling | 2.20E+00 | 7.14E−02 | CCND2, KAT2B, GADD45A, TOPBP1, BIRC5, CHEK2, DRAM1 |
| Oncostatin M Signaling | 2.18E+00 | 1.18E−01 | MAPK3, MMP13, OSMR, PLAU |
| Ceramide Degradation | 2.16E+00 | 3.33E−01 | NAAA, ASAH1 |
| Coagulation System | 2.14E+00 | 1.14E−01 | F2R, PLAUR, PLAU, PLAT |
| Cyclins and Cell Cycle Regulation | 2.11E+00 | 7.69E−02 | CCNA2, CCNE2, CCND2, WEE1, CCNB2, CDK1 |
| DNA damage-induced 14-3-3σ Signaling | 2.09E+00 | 1.58E−01 | CCNE2, CCNB2, CDK1 |
| Glioma Invasiveness Signaling | 2.06E+00 | 8.77E−02 | F2R, HMMR, MAPK3, PLAUR, PLAU |
| Inhibition of Matrix Metalloproteases | 1.97E+00 | 1.03E−01 | ADAM12, SDC2, MMP16, MMP13 |
| Sphingosine and Sphingosine-1-phosphate Metabolism | 1.90E+00 | 2.50E−01 | NAAA, ASAH1 |
| Bladder Cancer Signaling | 1.89E+00 | 6.90E−02 | FGF2, MMP16, MAPK3, VEGFB, MMP13, FGF5 |
| Role of BRCA1 in DNA Damage Response | 1.86E+00 | 7.81E−02 | FANCD2, RFC4, GADD45A, TOPBP1, CHEK2 |
| Hereditary Breast Cancer Signaling | 1.84E+00 | 6.09E−02 | CDC25C, FANCD2, RFC4, GADD45A, WEE1, CDK1, CHEK2 |
| Estrogen-mediated S-phase Entry | 1.81E+00 | 1.25E−01 | CCNA2, CCNE2, CDK1 |
| Factors Promoting Cardiogenesis in Vertebrates | 1.78E+00 | 6.52E−02 | TGFBR2, CCNE2, NOX4, CDC6, FZD1, ACVR2A |
| Granulocyte Adhesion and Diapedesis | 1.75E+00 | 5.08E−02 | IL36G, IL18, VCAM1, CCL2, CXCR4, SDC2, MMP16, ITGA6, MMP13 |

TABLE S2-continued

Top canonical pathways identified by Ingenuity Pathways Analysis to be different between EA mobilized equine cells and equine BM derived Mesenchymal Stem Cells

| Ingenuity Canonical Pathways | −log (p-value) | Ratio | Molecules |
|---|---|---|---|
| LXR/RXR Activation | 1.73E+00 | 5.79E−02 | ALB, IL36G, IL18, APoA1, CCL2, SAA1, SERPINF1 |
| UDP-N-acetyi-D-galactosamine Biosynthesis I | 1.65E+00 | 1.00E+00 | GALE |
| Clathrin-mediated Endocytosis Signaling | 1.64E+00 | 4.86E−02 | ALB, APOA1, IGF1, F2R, FGF2, DAB2, VEGFB, PDGFD, FGF5 |
| Agranuiocyte Adhesion and Diapedesis | 1.59E+00 | 4.76E−02 | IL36G, IL18, VCAM1, FN1, CCL2, CXCR4, MMP16, ITGA6, MMP13 |
| Human Embryonic Stem Cell Pluripotency | 1.52E+00 | 5.22E−02 | S1PR3, TGFBR2, BDNF, FGF2, FZD1, PDGFD, INHBA |
| Role of CHK Proteins in Cell Cycle Checkpoint Control | 1.47E+00 | 7.27E−02 | CDC25C, RFC4, CDK1, CHEK2 |
| Role of Macrophages, Fibroblasts and Endothelial Cells in Rheumatoid Arthritis | 1.45E+00 | 4.03E−02 | IL36G, IL18, VCAM1, FN1, SFRP2, CCL2, FGF2, MAPK3, VEGFB, MMP13, FZD1, PDGFD |
| Complement System | 1.44E+00 | 9.09E−02 | C1R, C1S, CFI |
| Inhibition of Angiogenesis by TSP1 | 1.41E+00 | 8.82E−02 | TGFBR2, GUCY1A3, SDC2 |
| Ephrin Receptor Signaling | 1.39E+00 | 4.60E−02 | PAK1, ANGPT1, CXCR4, SDC2, MAPK3, VEGFB, GNA14, PDGFD |
| IL-17A Signaling in Fibroblasts | 1.37E+00 | 8.57E−02 | CCL2, MAPK3, NFKBIZ |
| Taurine Biosynthesis | 1.36E+00 | 5.00E−01 | CDO1 |

TABLE S3

Significantly down-regulated genes in EA-mobillzed MSC as compared to BM-MSC and ADSC.

| GeneSymbol* | Gene ID | Fold-Change (EA vs. BM) | p-value (EA vs. BM) | Fold-Change (EA vs. ADSC) | p-value (EA vs. ADSC) |
|---|---|---|---|---|---|
| HP | 15069510 | −163.90 | 1.56E−07 | −1.48 | 7.91E−02 |
| SAA1 | 15112997 | −64.48 | 7.55E−04 | −1.93 | 3.58E−01 |
| JAM2 | 15053764 | −51.87 | 9.30E−07 | 3.07 | 1.19E−03 |
| GMFG | 14954018 | −37.56 | 5.49E−07 | −50.36 | 3.46E−07 |
| C1S | 15095794 | −37.33 | 8.79E−04 | −6.72 | 1.83E−02 |
| SLPI | 15040462 | −36.46 | 9.34E−05 | 2.24 | 8.49E−02 |
| VCAM1 | 15092613 | −31.42 | 2.98E−03 | −2.52 | 2.44E−01 |
| C1R | 15100117 | −26.62 | 1.18E−03 | −10.85 | 5.71E−03 |
| FAP | 15009547 | −25.16 | 2.60E−04 | −6.27 | 4.80E−03 |
| CDO1 | 14983389 | −18.89 | 1.54E−03 | −1.64 | 3.91E−01 |
| IGF2 | 14974243 | −18.43 | 5.06E−05 | −1.75 | 9.61E−02 |
| GPM6B | 15130778 | −18.18 | 6.48E−05 | −3.61 | 4.88E−03 |
| SFRP2 | 15020345 | −17.72 | 1.10E−02 | 3.33 | 1.80E−01 |
| RGCC | 15005251 | −14.91 | 3.06E−03 | −6.66 | 1.53E−02 |
| FCER1G | 15085566 | −14.74 | 4.37E−04 | −7.75 | 1.84E−03 |
| RANBP3L | 15033729 | −11.80 | 5.94E−04 | −3.10 | 2.35E−02 |
| GPC3 | 15133448 | −11.08 | 2.42E−02 | 1.09 | 9.17E−01 |
| ITGBL1 | 15003944 | −10.79 | 1.93E−04 | −53.25 | 1.02E−05 |
| ANGPT1 | 15124168 | −10.39 | 3.78E−02 | −5.60 | 9.85E−02 |
| NMES1 | 14946865 | −9.71 | 2.97E−04 | 1.14 | 6.80E−01 |
| SDC2 | 15121830 | −9.15 | 1.70E−03 | 1.38 | 4.67E−01 |
| EPHX1 | 15074204 | −8.66 | 1.41E−03 | −11.76 | 7.02E−04 |
| ISLR | 14945891 | −8.52 | 2.53E−05 | 1.17 | 4.38E−01 |
| HOXC6 | 15097359 | −8.38 | 1.97E−04 | −5.83 | 5.50E−04 |
| APOA1 | 15109786 | −8.35 | 2.05E−03 | −4.78 | 8.79E−03 |
| HOXC8 | 15097357 | −8.29 | 2.65E−06 | −1.48 | 1.94E−02 |
| FBLN5 | 15047891 | −8.06 | 1.07E−04 | −4.43 | 6.85E−04 |
| ATP6V0D2 | 15123017 | −7.78 | 2.37E−03 | −1.27 | 5.76E−01 |
| GBP6 | 15088271 | −7.54 | 6.39E−04 | −10.73 | 3.74E−02 |
| PTGFR | 15093253 | −7.15 | 4.76E−03 | 1.51 | 3.93E−01 |
| RFTN1 | 14997779 | −7.02 | 6.92E−05 | −1.27 | 2.74E−01 |
| FKBP1B | 14994284 | −6.98 | 2.57E−04 | −1.60 | 1.14E−01 |
| GPX3 | 14985179 | −6.89 | 7.00E−03 | −12.52 | 1.91E−03 |
| EFEMP1 | 14989529 | −6.43 | 9.94E−03 | −4.19 | 2.89E−02 |
| ACSS3 | 15058037 | −6.30 | 6.23E−05 | 1.31 | 1.96E−01 |
| LRRC17 | 15076581 | −6.27 | 4.14E−02 | −3.81 | 1.09E−01 |
| TPST1 | 14978943 | −6.13 | 9.38E−04 | −2.38 | 2.79E−02 |
| FAM180A | 15082978 | −6.01 | 1.45E−02 | −1.38 | 5.64E−01 |
| EDIL3 | 14983877 | −5.98 | 3.13E−03 | 3.95 | 1.07E−02 |
| FABP4 | 15120866 | −5.97 | 9.43E−02 | −53.83 | 4.43E−03 |
| SEPP1 | 15033431 | −5.86 | 1.58E−02 | −18.48 | 1.53E−03 |
| CX43 | 14953019 | −5.85 | 4.99E−06 | 1.75 | 2.93E−03 |
| PDGFRL | 15056268 | −5.60 | 1.86E−03 | −11.17 | 2.76E−04 |
| ANO5 | 15108201 | −5.37 | 5.40E−05 | 1.51 | 4.72E−02 |
| SLC29A1 | 15028956 | −5.32 | 2.73E−03 | −3.34 | 1.24E−02 |
| CXCR7 | 15094905 | −5.30 | 7.02E−03 | 1.50 | 3.66E−01 |
| FAM13C | 14943001 | −5.28 | 2.41E−04 | 1.05 | 8.12E−01 |
| CP | 15002207 | −5.27 | 8.97E−03 | −1.39 | 4.81E−01 |
| DUSP10 | 15074370 | −5.21 | 1.82E−02 | 1.01 | 9.90E−01 |
| CFI | 15021118 | −5.17 | 4.12E−05 | −1.50 | 3.06E−01 |
| SLIT2 | 15072160 | −5.02 | 6.71E−07 | 1.01 | 9.39E−01 |
| OXCT1 | 15033445 | −4.94 | 2.06E−03 | −8.92 | 3.96E−04 |
| ECM2 | 15042573 | −4.92 | 2.14E−03 | −1.05 | 8.90E−01 |
| COLEC12 | 15119586 | −4.90 | 3.58E−06 | −4.02 | 7.86E−06 |
| RFTN2 | 15011006 | −4.90 | 4.34E−02 | −1.01 | 9.88E−01 |
| OSMR | 15035684 | −4.57 | 2.73E−05 | −3.41 | 9.33E−05 |
| ANTXR1 | 14992709 | −4.52 | 2.64E−04 | −1.56 | 6.42E−02 |
| KITLG | 15060149 | −4.51 | 1.10E−03 | 1.17 | 5.62E−01 |
| IFNGR2 | 15053898 | −4.50 | 9.24E−04 | −4.23 | 1.15E−03 |
| ABI3BP | 15013425 | −4.50 | 3.55E−02 | −31.57 | 8.10E−04 |
| EMP1 | 15096050 | −4.47 | 2.70E−02 | −5.51 | 1.54E−02 |
| NREP | 14983481 | −4.46 | 3.69E−04 | 2.34 | 6.44E−03 |
| NDUFA4L2 | 15102950 | −4.41 | 1.83E−01 | 6.00 | 1.19E−01 |
| LY6E | 15122687 | −4.40 | 1.32E−02 | −3.47 | 2.66E−02 |
| SAA | 15113003 | −4.32 | 1.56E−06 | −1.05 | 8.03E−01 |
| ZNF449 | 15130042 | −4.31 | 8.94E−05 | −1.91 | 6.35E−03 |
| SERPINF1 | 14962303 | −4.30 | 1.04E−02 | −2.70 | 4.67E−02 |
| PRSS35 | 14952352 | −4.19 | 3.68E−04 | 3.25 | 1.05E−03 |
| RSPO3 | 14953119 | −4.18 | 9.00E−04 | 1.47 | 1.52E−01 |
| CTSC | 15106627 | −4.18 | 3.36E−04 | 1.35 | 1.73E−01 |

TABLE S3-continued

Significantly down-regulated genes in EA-mobilzed MSC as compared to BM-MSC and ADSC.

| GeneSymbol* | Gene ID | Fold-Change (EA vs. BM) | p-value (EA vs. BM) | Fold-Change (EA vs. ADSC) | p-value (EA vs. ADSC) |
|---|---|---|---|---|---|
| GPR183 | 15005810 | −4.15 | 3.49E−03 | 1.65 | 1.54E−01 |
| HNMT | 15006605 | −4.15 | 6.14E−02 | −10.28 | 9.42E−03 |
| SMOC1 | 15045019 | −4.13 | 3.87E−03 | 2.22 | 4.29E−02 |
| NT5E | 14952379 | −4.05 | 5.00E−03 | −1.14 | 6.98E−01 |
| INSIG1 | 15080042 | −4.01 | 4.27E−03 | −4.38 | 3.16E−03 |
| CXCR4 | 15008961 | −3.88 | 2.76E−02 | 1.28 | 6.19E−01 |

*Only annotated, unique genes from the chip are presented.

TABLE S4

Characteristics of the horses used in the study (G = Gelding, F = Female)

| Horse | Age | Gender | Breed |
|---|---|---|---|
| 1 | 23 | G | Swedish Warmblood |
| 2 | 8 | G | Dutch Warmblood |
| 3 | 13 | G | Oldenberg |
| 4 | 9 | F | Thoroughbred |
| 5 | 19 | G | Hannoverian |
| 6 | 14 | G | Dutch Warmblood |
| 7 | 11 | G | Duch Warmblood |
| 8 | 12 | G | Westfalian |
| 9 | 18 | G | Half-thoroughbred/half Dutch Warmblood |
| 10 | 16 | F | Half-thoroughbred/half Dutch Warmblood |
| 11 | 15 | G | Dutch Warmblood |
| 12 | 12 | F | Danish Warmblood |

TABLE S5

Primers used for the qRT-PCR validation of microarray data

| Gene symbol | RefSeq | Forward primer | Reverse primer |
|---|---|---|---|
| ADAM23 | XM_001918018 | GCCGAAAGCCAAAATGTGA | CCGTTTCCTCCATGATGCA |
| CD63 | XM_001504778 | TCAGGGCTGCGGGACTAAG | TCCACACAGCCCTTGGTATAGA |
| COL1A1 | AF034691 | TGGCCTCGGAGGAAACTTT | GCACGGAAATTCCAGCAAAT |
| ENG | XM_001500078 | TGTCTTGCGCAGCACCTACT | GACCACCTCATTACTGACCACATTT |
| FGF5 | XM_001492556 | CGGGACGGGAGTGGTATGT | TGCAGCCTCGCTTAGCTTTC |
| GCNT4 | XM_005599736 | CGTATCGCCACGAACTCAGA | TCGTCCTCACGGGAAGCTT |
| HP | XM_001497810 | GCGCAGTGAAGGAGATGGA | TGGCCTTATTTACCCACTGCTT |
| IGFBP3 | XM_001496239 | AGAACTTCTCCTCCGAGTCCAA | TTCAGGAACTTGAGGTGGTTCA |
| NDUFA7 | XM_001497139 | ATCGTCATGTCCTCACAGAAGGT | CGTCACCGCCTTCTTCTCA |
| RLN | NM_001081809 | GGGACAACCCGTAGAAATTGTG | CAACTTCGTATTTAAAGCTTCTGCAT |
| RPL17 | NM_003365546 | TGCCACATCGAGATGATCCTT | GCAACCTCCTCTTCTGGTTTAGG |
| SAA1 | NM_001163892 | GCGCCTGGGCTGCTAAA | GGCCACTGTCTCCAAACTTGA |
| SERPINB2 | XM_003365564 | CCCAAACCAAAGGCAAAATC | TCCTGGTGTCCCCATCTACAG |

What is claimed is:

1. A method of increasing mesenchymal stem cells in the circulating blood of a mammal comprising contacting two or more acupuncture points of the group consisting of LI-4, LI-11, GV-14, and GV-20 of the mammal with a therapeutically effective amount of electroacupuncture stimulation to mobilize mesenchymal stem cells into the circulating blood of the mammal.

2. The method of claim 1, wherein the therapeutically effective amount of electroacupuncture stimulation is from about 15-25 hz for 10 to 60 minutes.

3. The method of claim 1, wherein the mammal is selected is selected from the group consisting of: humans, horses, rats, and mice.

4. A method of isolating mesenchymal stem cells from the peripheral blood of a mammal to yield electroacupuncture-mobilized mesenchymal stem cells comprising the steps of:
  (a) contacting two or more acupuncture points from the group consisting of LI-4, LI-11, GV-14, and GV-20 in the mammal with a therapeutically effective amount of electroacupuncture-induced stimulation;
  (b) collecting the peripheral blood from the mammal after stimulation;
  (c) separating peripheral blood mononuclear cells from the blood and exposing the cells to conditions that generate formation of mesenchymal colonies.

5. The method of claim 4, wherein said conditions that promote mesenchymal stem cell formation comprise culturing said peripheral blood mononuclear cells in the presence of a combination of Ham's F-12 and DMEM in a 1:1 ratio optionally with 15% Fetal Bovine Serum.

6. The method of claim 4, wherein the electroacupuncture is applied for 20-50 minutes.

7. The method of claim 4, wherein the electroacupuncture is applied at 0.5-3.5 mA.

8. The method of claim 4, further comprising treating damaged tissue in a mammal by contacting the damaged tissue with mesenchymal stem cells of claim 7, wherein said contacting is by direct injection into the area of the damaged tissue, intraparentoneal injection, intramuscular injection, or by intravenous injection.

9. The method of claim 8, wherein said damaged tissue is the result of injury, or trauma, or disease.

10. The method of claim 8, wherein the damaged tissue is a damaged tendon.

11. A method of treating damaged tissue or inflammation in a mammal, the method comprising increasing mesenchymal stem cells in the circulating blood of a mammal by contacting two or more acupuncture points selected from the group consisting of LI-4, LI-11, GV-14, and GV-20 of the mammal with a therapeutically effective amount of electroacupuncture stimulation to mobilize mesenchymal stem cells into the circulating blood of the mammal.

12. The method of claim 11 wherein electroacupuncture is applied at 15-25 Hz for 10-60 minutes.

13. The method of claim 11, wherein the electroacupuncture is applied at 0.5-3.5 Ma.

14. The method of claim 11, wherein electroacupuncture stimulation is applied simulataneously to acupuncture points LI-4, LI-11, GV-14 and GV-20.

* * * * *